(12) United States Patent
Veraitch et al.

(10) Patent No.: US 11,993,765 B2
(45) Date of Patent: May 28, 2024

(54) CELL CULTURE DEVICE SYSTEM AND METHODS OF USE THEREOF

(71) Applicant: ORIBIOTECH LTD, London (GB)

(72) Inventors: Farlan Veraitch, London (GB); Christopher Mason, Cambridge, MA (US)

(73) Assignee: Silicon Valley Bank UK Limited, London (GB)

( * ) Notice: Subject to any disclaimer, the term of this patent is extended or adjusted under 35 U.S.C. 154(b) by 911 days.

(21) Appl. No.: 16/349,051

(22) PCT Filed: Nov. 10, 2017

(86) PCT No.: PCT/GB2017/053389
§ 371 (c)(1),
(2) Date: May 10, 2019

(87) PCT Pub. No.: WO2018/087558
PCT Pub. Date: May 17, 2018

(65) Prior Publication Data
US 2020/0190457 A1 Jun. 18, 2020

(30) Foreign Application Priority Data
Nov. 11, 2016 (GB) ..................... 1619152

(51) Int. Cl.
*C12M 3/00* (2006.01)
*B65D 51/28* (2006.01)
(Continued)

(52) U.S. Cl.
CPC ............ *C12M 23/44* (2013.01); *C12M 23/26* (2013.01); *C12M 41/12* (2013.01); *C12Q 1/02* (2013.01); *B65D 51/2864* (2013.01)

(58) Field of Classification Search
None
See application file for complete search history.

(56) References Cited

U.S. PATENT DOCUMENTS 4,441,996 A * 4/1984 Hurst ...................... C02F 1/002
222/215
4,867,172 A 9/1989 Haber et al.
(Continued)

FOREIGN PATENT DOCUMENTS

| EP | 1491623 A1 | 12/2004 |
| GB | 2080756 A | 2/1982 |

(Continued)

OTHER PUBLICATIONS

Document entitled: KR20140120433A Method for Cultivating Mass Microalgae Using Photobioreactors With the Function of Controlling Light-Receiving Area, machine translation of KR20140120433A provided by Espacenet, original document published Oct. 14, 2014 (Year: 2014).*

(Continued)

*Primary Examiner* — Holly Kipouros
(74) *Attorney, Agent, or Firm* — Morgan, Lewis & Bockius LLP

(57) ABSTRACT

A container for use in growing, culturing and/or modifying cells has a primary container (10) and defines an internal lumen in which a wall element (8) of the primary container (10) is compressible, and wherein the container has an auxiliary container (16) in fluid communication with the primary container (10). The fact that the device has an auxiliary container 16 allows a number of separate reactions to be carried out within a single container.

8 Claims, 26 Drawing Sheets

(51) Int. Cl.
*C12M 1/00* (2006.01)
*C12M 1/34* (2006.01)
*C12Q 1/02* (2006.01)

(56) References Cited

U.S. PATENT DOCUMENTS

| | | | | |
|---|---|---|---|---|
| 6,121,042 | A * | 9/2000 | Peterson | C12M 41/00 |
| | | | | 435/284.1 |
| 11,242,506 | B2 * | 2/2022 | Davidzon | C12M 27/02 |
| 2002/0104265 | A1 * | 8/2002 | Miersch | C12P 5/023 |
| | | | | 48/127.3 |
| 2003/0143727 | A1 * | 7/2003 | Chang | C12M 23/26 |
| | | | | 435/289.1 |
| 2003/0198406 | A1 | 10/2003 | Bibbo et al. | |
| 2006/0278156 | A1 * | 12/2006 | Miller | A47G 23/14 |
| | | | | 73/149 |
| 2007/0224676 | A1 * | 9/2007 | Haq | C12M 41/44 |
| | | | | 435/298.2 |
| 2007/0254356 | A1 | 11/2007 | Wilson et al. | |
| 2008/0022786 | A1 * | 1/2008 | Sann | G01N 1/2042 |
| | | | | 73/863.86 |
| 2008/0118974 | A1 * | 5/2008 | Martin | C12M 29/04 |
| | | | | 435/297.1 |
| 2009/0236338 | A1 | 9/2009 | Elton et al. | |
| 2010/0203624 | A1 * | 8/2010 | Singh | B01F 35/531 |
| | | | | 435/289.1 |
| 2010/0209966 | A1 * | 8/2010 | Everett | C12M 23/44 |
| | | | | 435/303.1 |
| 2013/0157355 | A1 | 6/2013 | Barrett et al. | |
| 2015/0252317 | A1 * | 9/2015 | Lipkens | C12M 41/44 |
| | | | | 210/748.05 |
| 2016/0040109 | A1 | 2/2016 | Dahlberg et al. | |
| 2016/0095279 | A1 | 4/2016 | Brown | |
| 2016/0201023 | A1 | 7/2016 | Tajima | |

FOREIGN PATENT DOCUMENTS

| | | | | |
|---|---|---|---|---|
| JP | 2006314276 | A * | 11/2006 | C12M 23/04 |
| JP | 2017-195857 | A | 11/2017 | |
| KR | 1020050028919 | | 3/2005 | |
| KR | 20130036060 | A * | 10/2014 | |
| WO | WO 2004/037969 | A2 | 5/2004 | |
| WO | WO 2008/030597 | A2 | 3/2008 | |
| WO | WO 2008/089510 | A1 | 7/2008 | |
| WO | WO 2016/185221 | A1 | 11/2016 | |
| WO | WO 2015/037468 | A1 | 3/2017 | |

OTHER PUBLICATIONS

Document entitled "JP2006314276A Cell Culture Container", machine translation of JP 2006314276 A provided by Espacenet, original document published 2016 (Year: 2016).*

Office Action in corresponding application No. No. JP 2019-547193, dated Mar. 1, 2021.

* cited by examiner

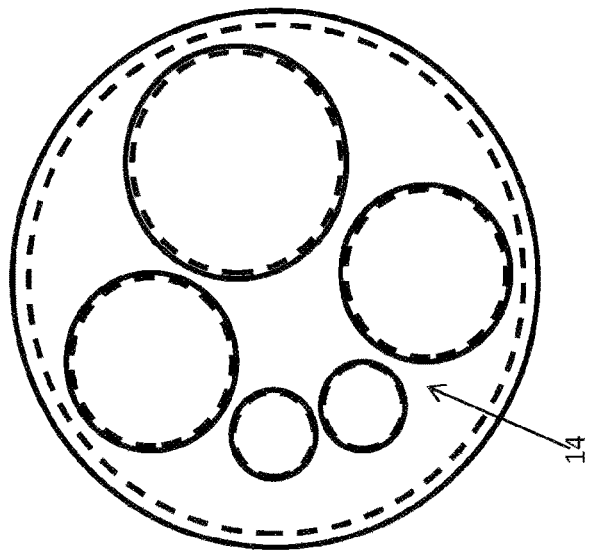
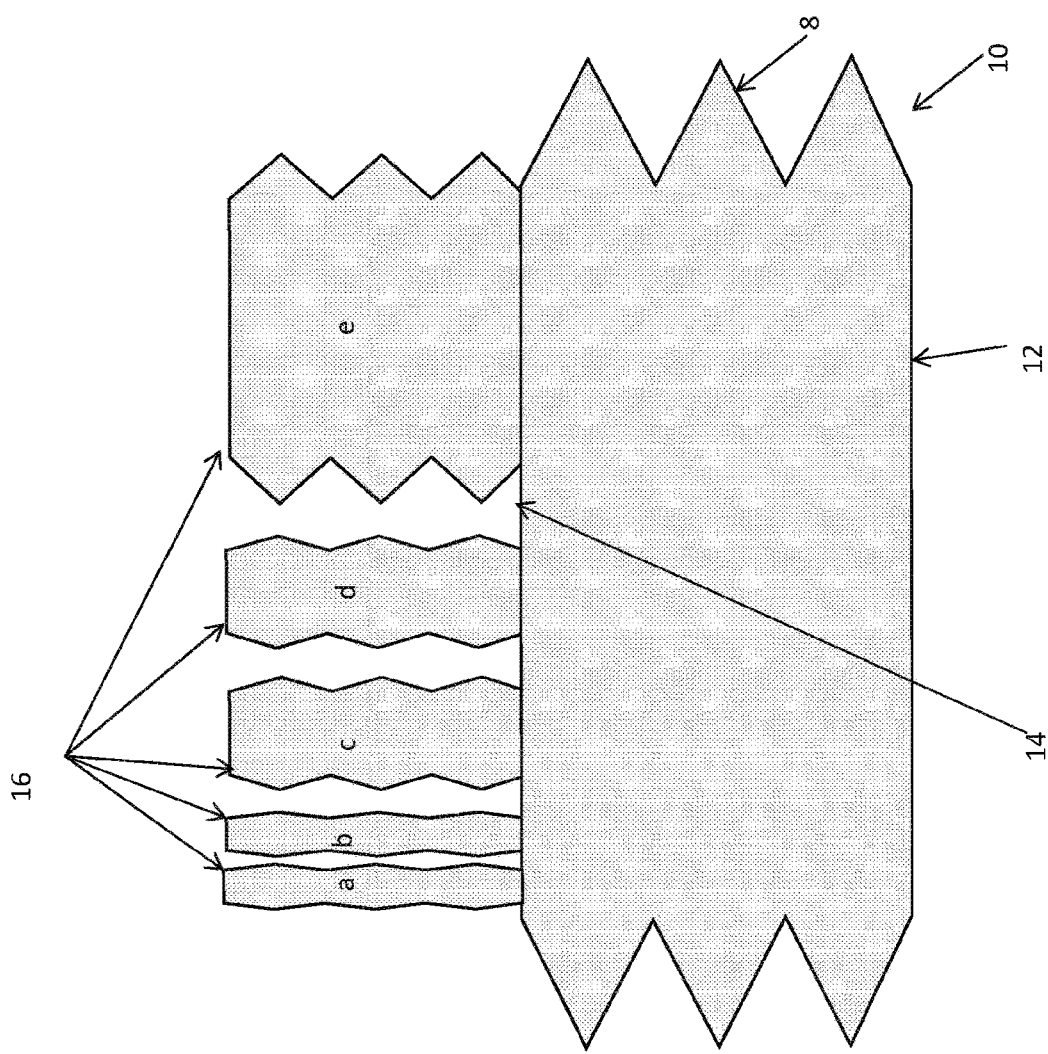
FIGURE 1(a)
FIGURE 1(b)

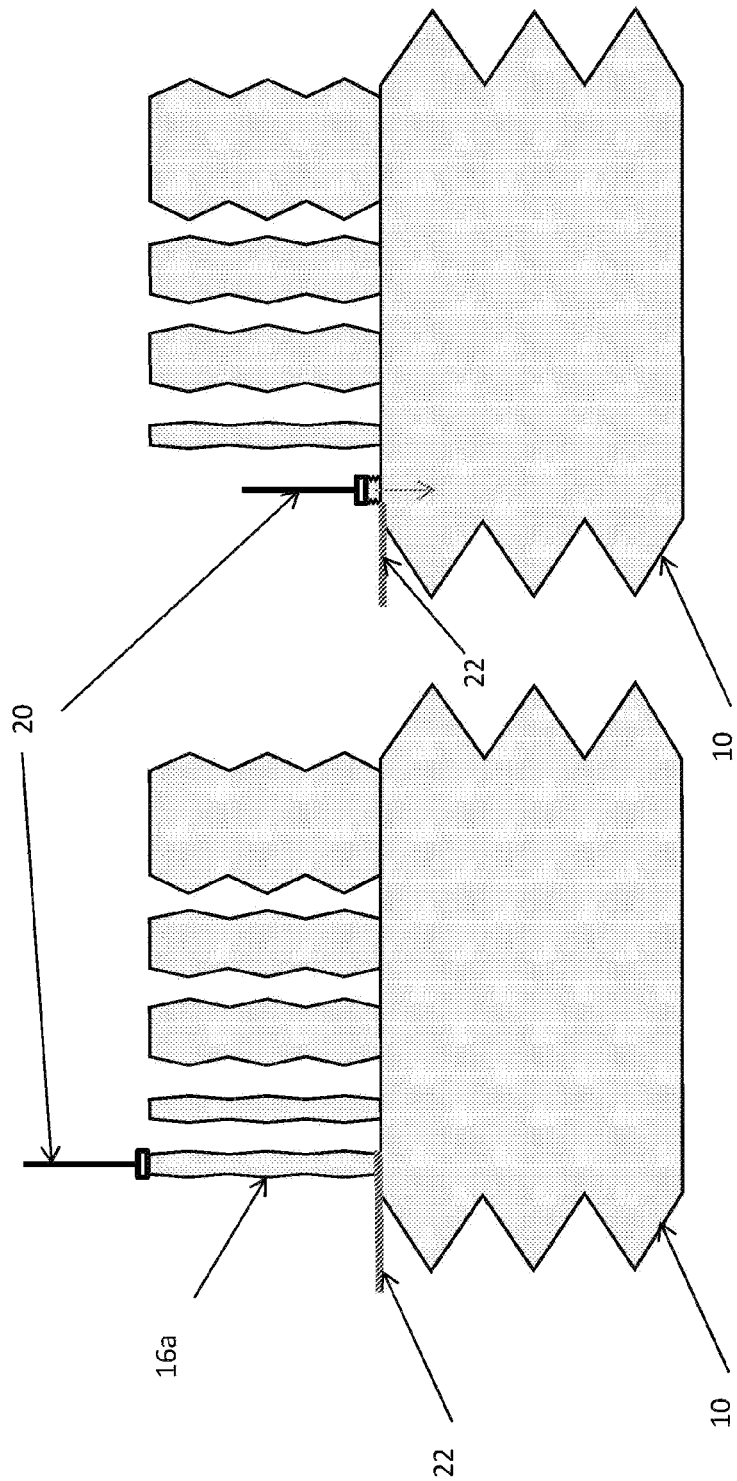

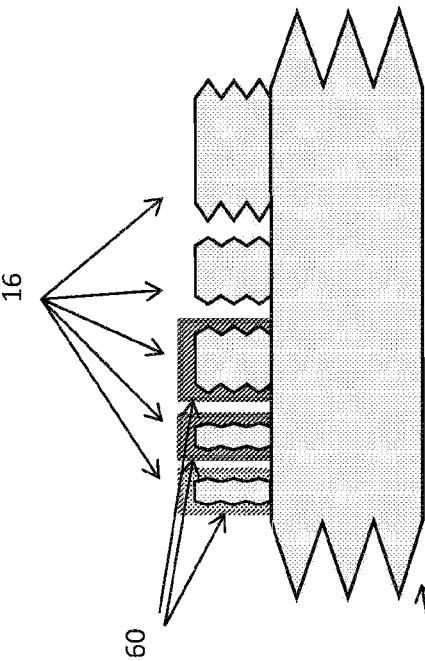
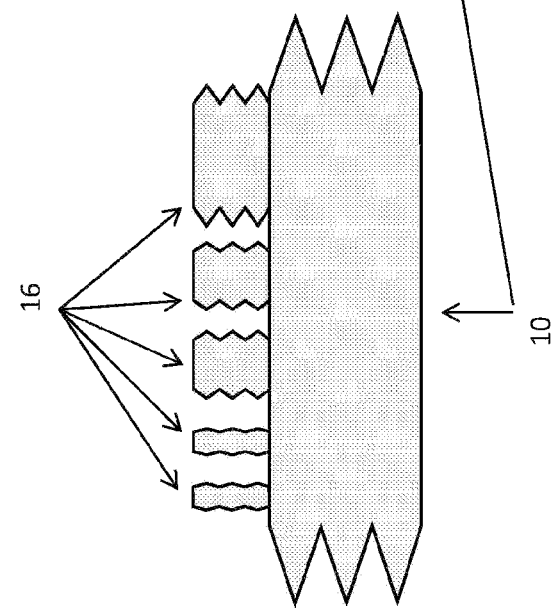

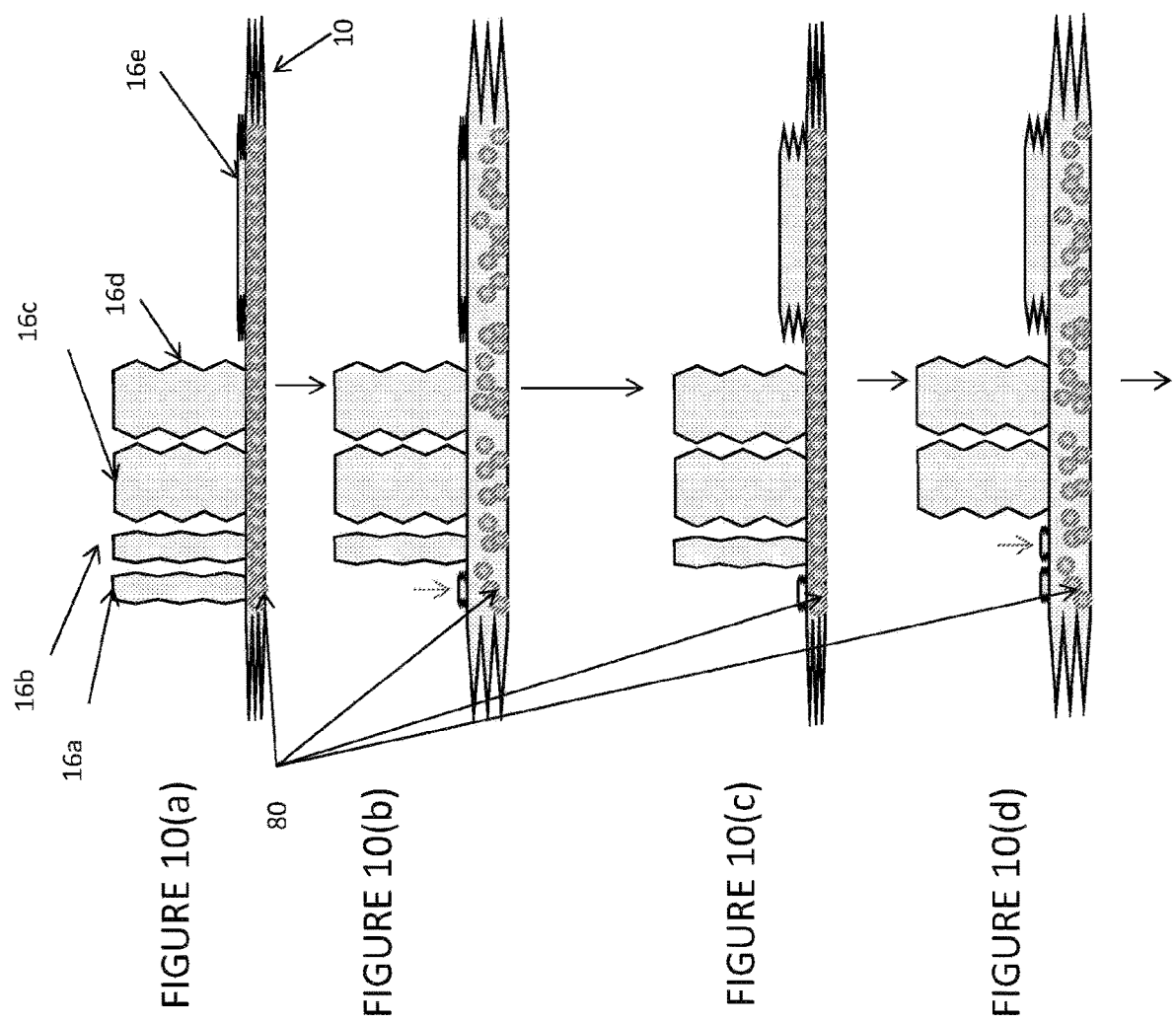

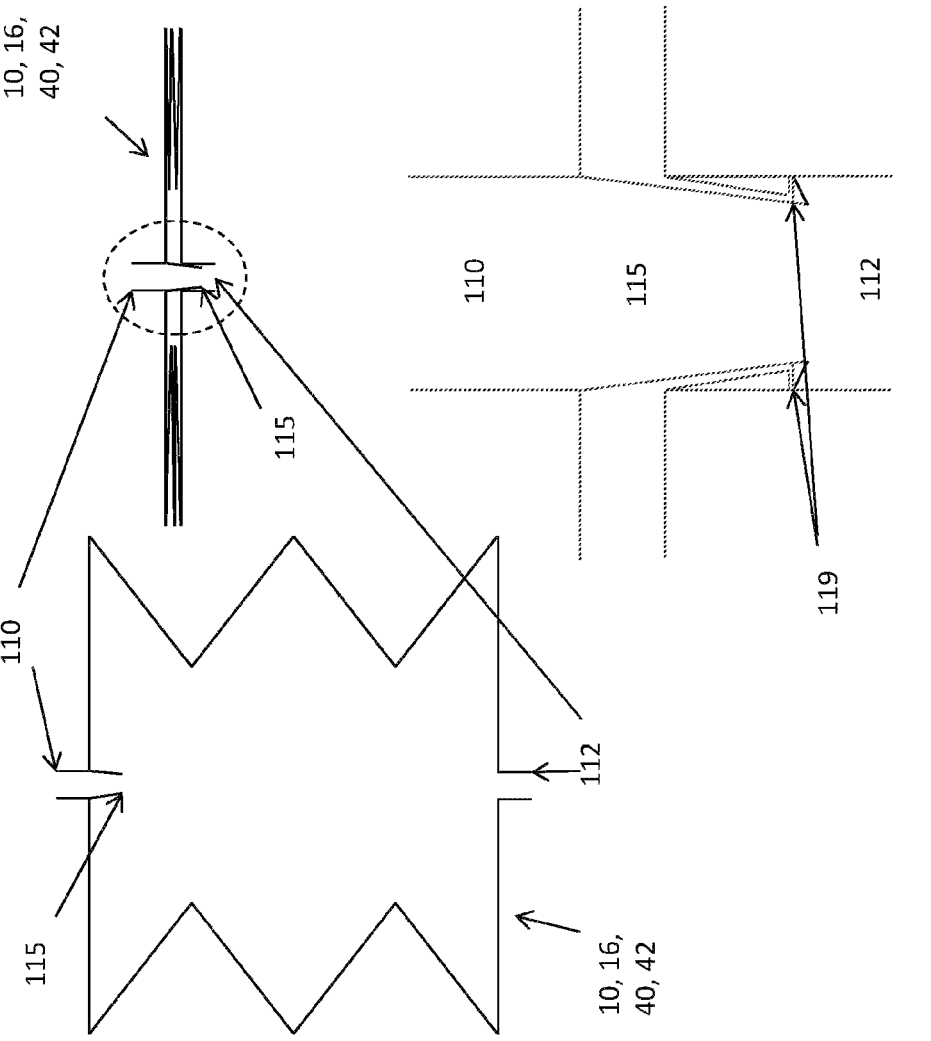

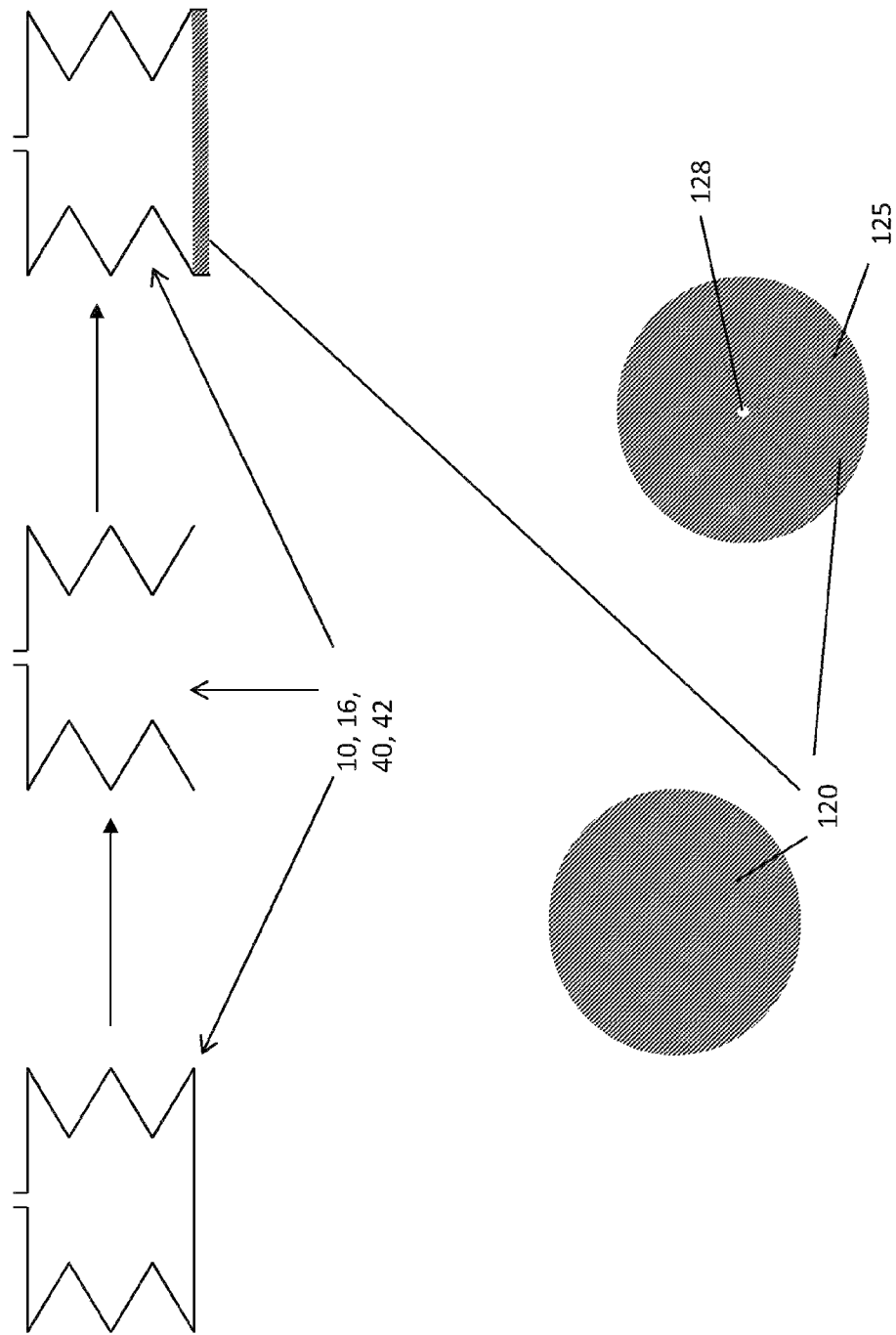

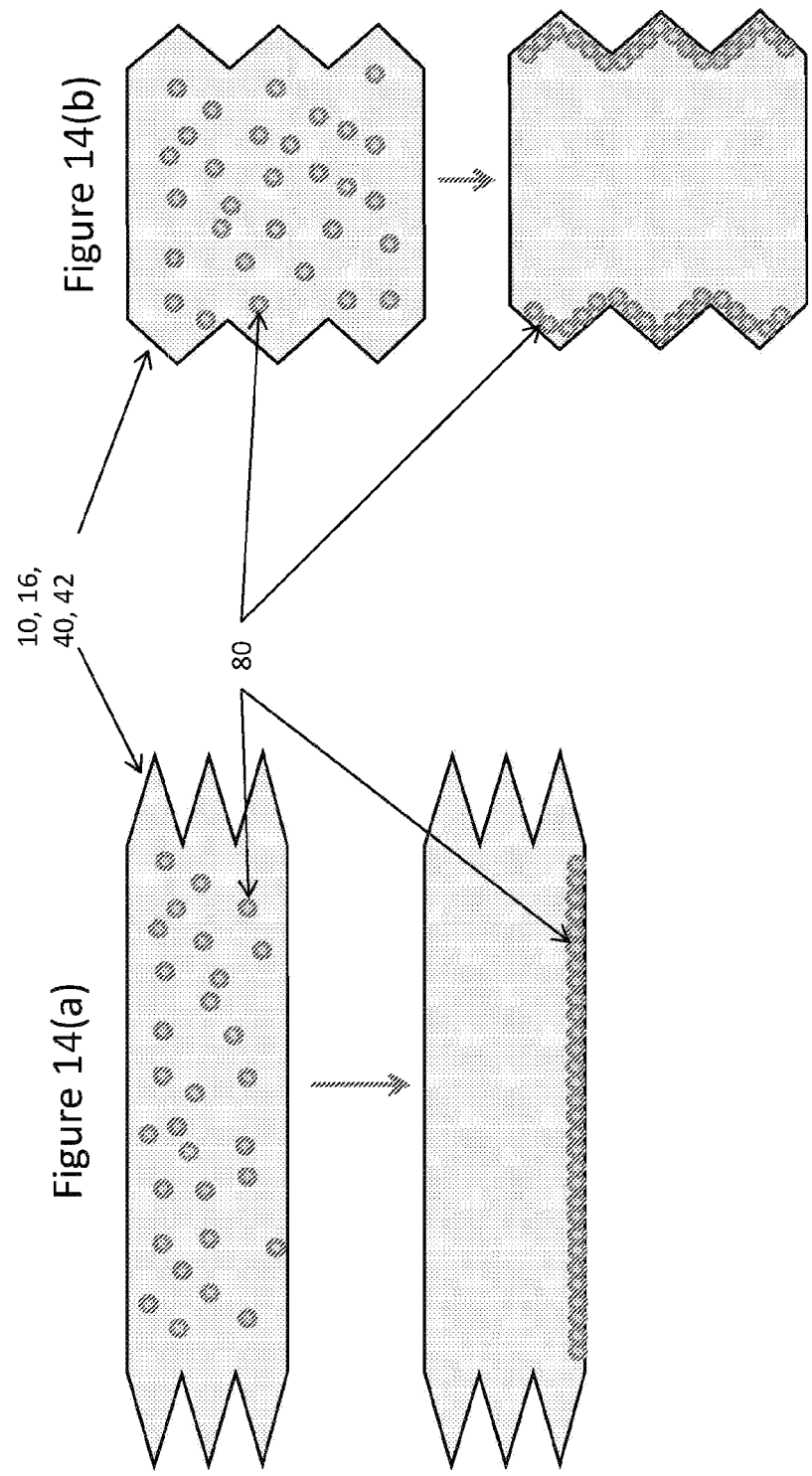

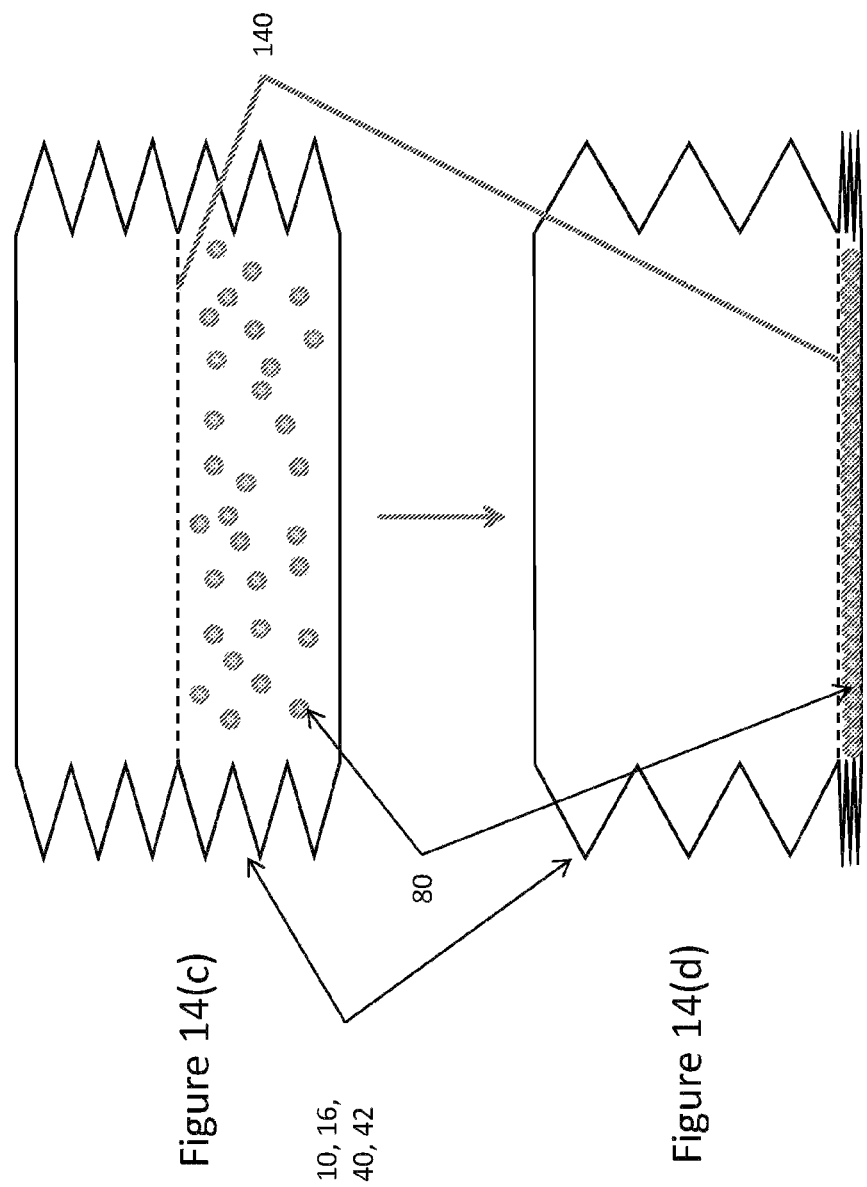

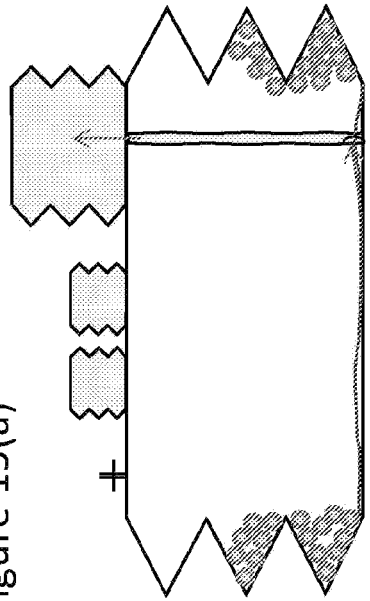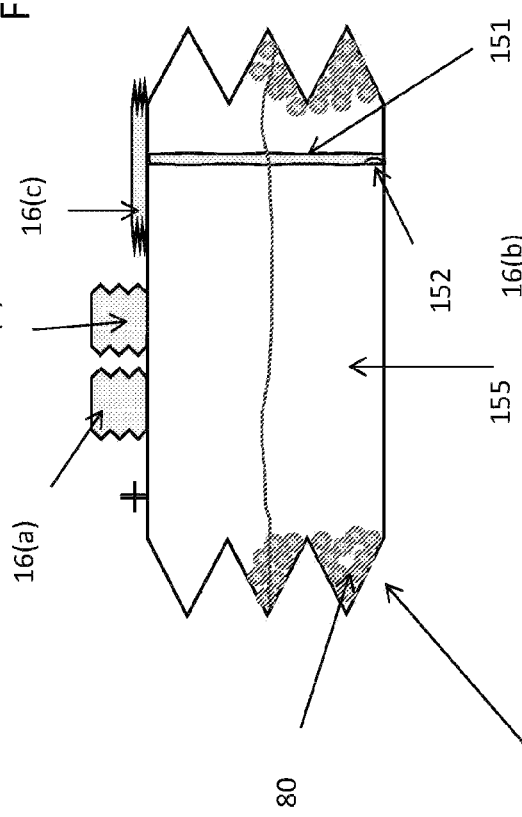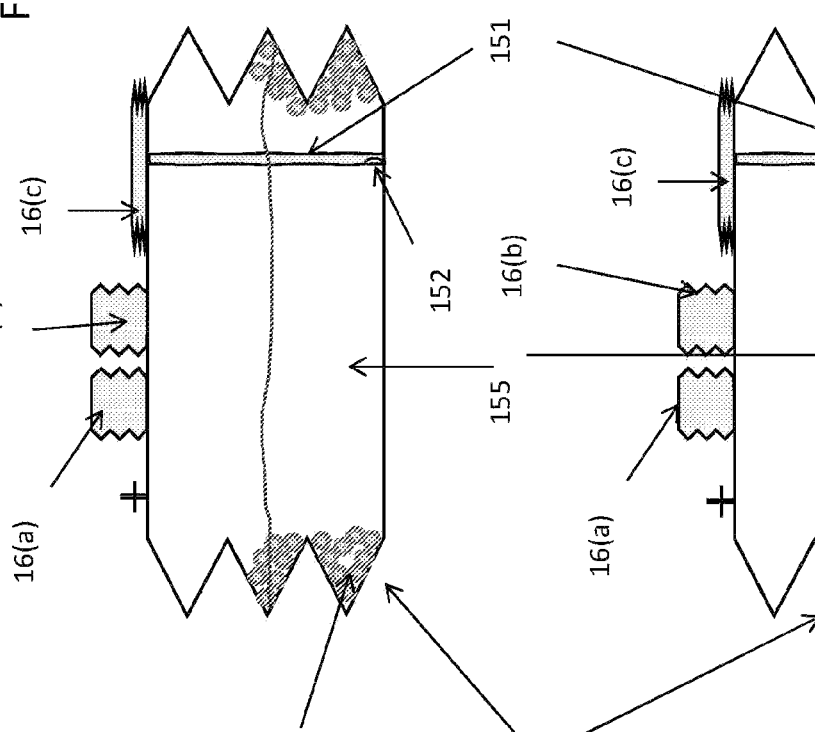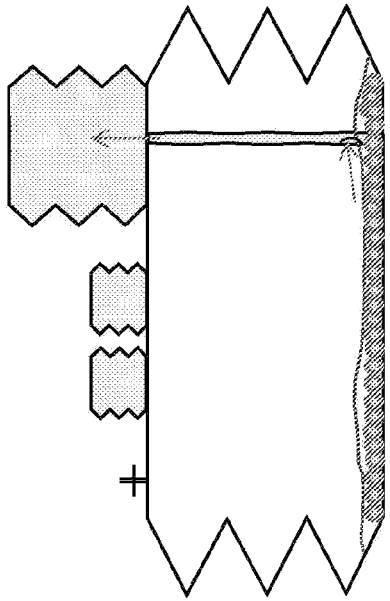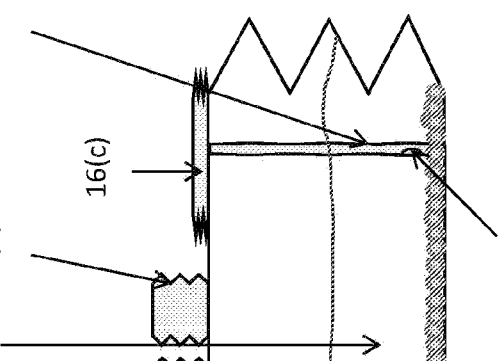

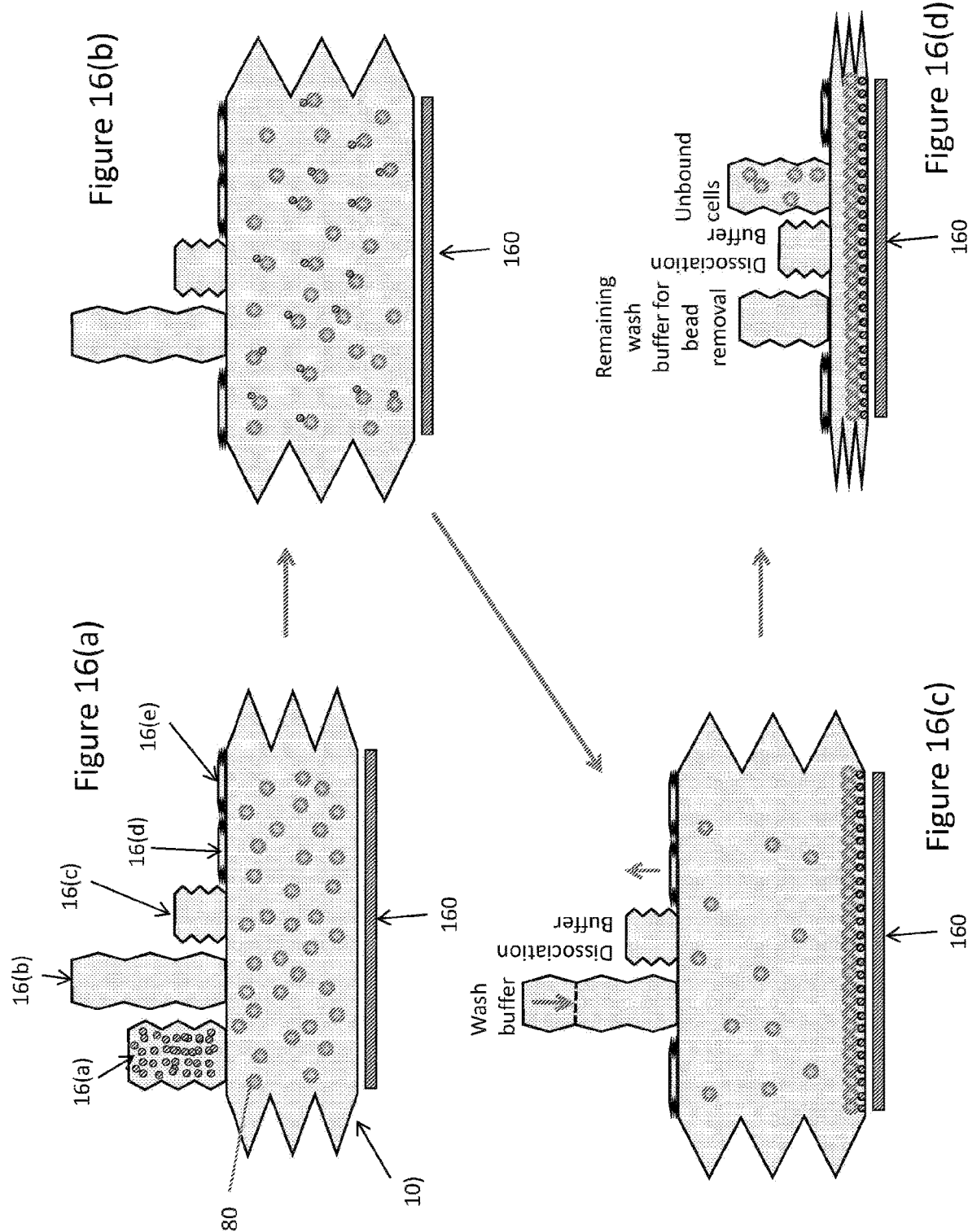

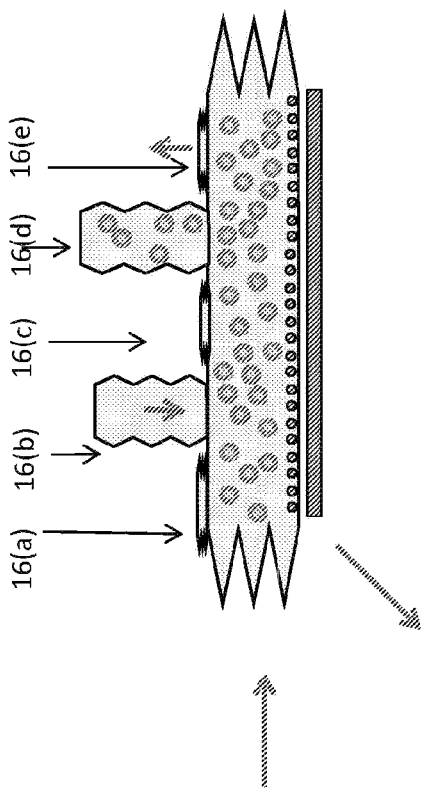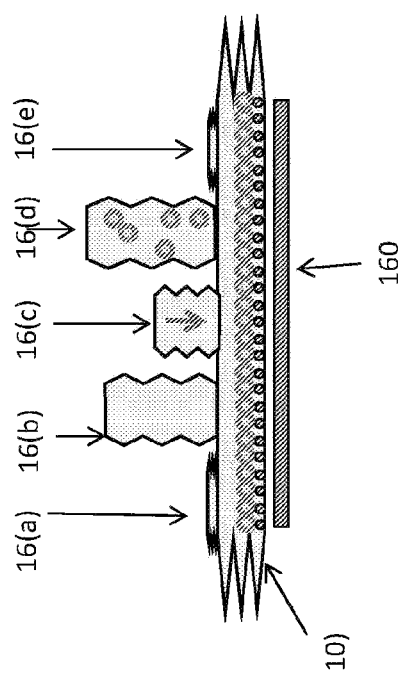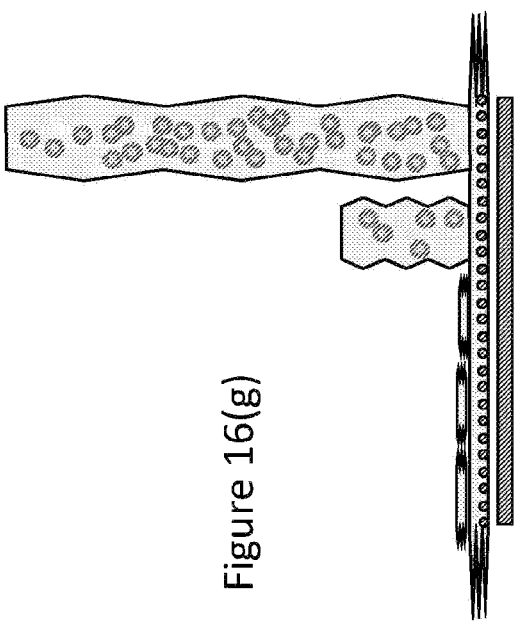

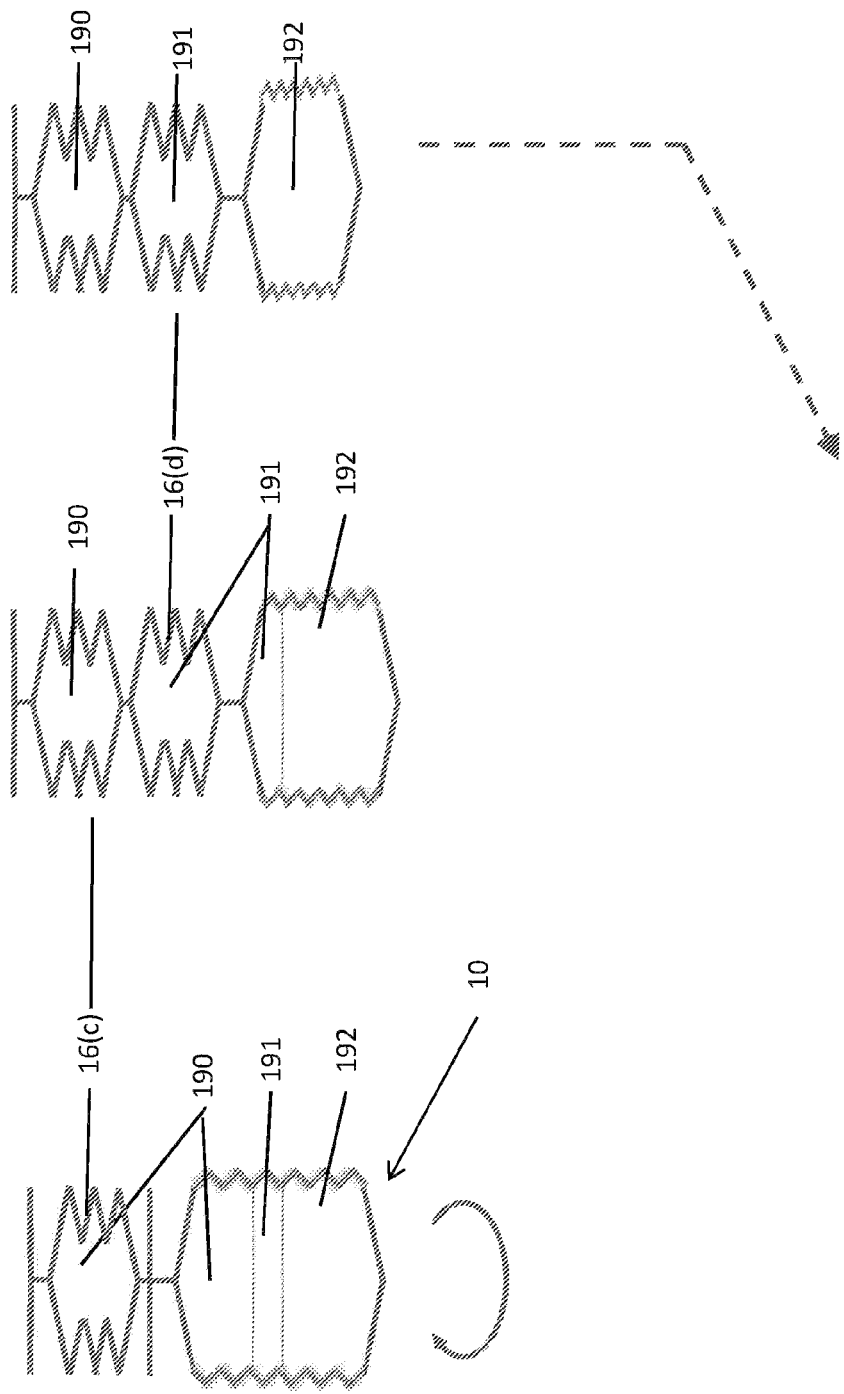

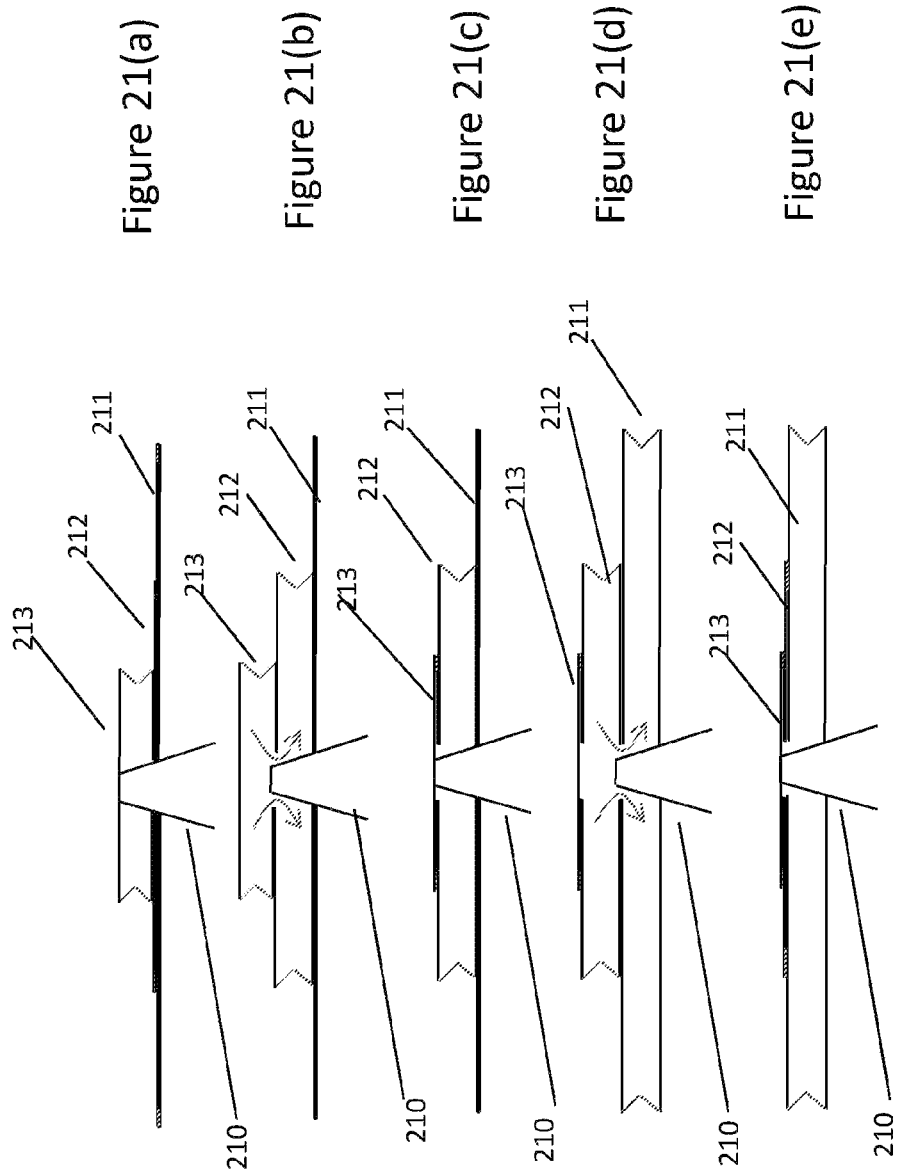

CELL CULTURE DEVICE SYSTEM AND METHODS OF USE THEREOF

CROSS-REFERENCE TO RELATED APPLICATIONS

This application is a US National Phase of International Patent Application No. PCT/GB2017/053389, filed Nov. 10, 2017, which claims priority to United Kingdom Patent Application No. 1619152.0, filed on Nov. 11, 2016, the disclosures of which are incorporated herein in their entirety for all purposes.

The present invention relates to a device for culturing, manipulating or storing cells, including systems using such devices and methods of use thereof. The invention relates to methods of expansion of cells in culture, genetic modification and cryopreservation, as well as to methods of delivery of cells to subjects, including methods of obtaining a biological sample using such devices.

The culture or processing of cells typically requires the use of a device to hold the cells, for example in an appropriate culture medium when culturing the cells. The known devices include shaker flasks, roller bottles, T-flasks and bags. Such bottles or flasks are widely used but suffer from several drawbacks. Chief among the problems are the requirement for transfer of cells without contamination when passaging or processing subsequently and the sterile addition of supplements and factors.

The existing cell culture devices require re-supply of culture medium and oxygen for continued cell growth. Gas permeable cell culture devices are described in U.S. Pat. No. 8,415,144. However, such devices also require transfer of medium and/or cells in and out of the devices.

Collapsible devices for use in medicine are known; see for example U.S. Pat. No. 4,867,172 concerning a blood collector, or WO 2008/030597 concerning a canister liner for fluid collection. However, such devices are not fabricated or constructed for use in cell culture.

A key limiting factor in the production of cells for use in medicine is the absence of fully closed systems for processing of cells without contamination. For example during culture or subsequent processing of cells there is a risk of contamination when making additions to the culture vessel, or when removing cells. The operating systems are largely manual and hence expensive to operate. Furthermore with increasing manual operations comes increasing risk of manual errors and therefore the current labour-intensive processes lack the robustness required for the manufacture of clinical-grade therapeutics.

There is therefore a need for cell culture devices which permit such processing which avoids the requirement for constant passaging of cells into fresh culture devices, multiple transfer of cells to and from centrifuge tubes, enables easy genetic modification of cells and simplifies handling of the cells in subsequent steps (such as washing etc.) and/or clinical use. For example, it would be advantageous if scale-up of cells in culture could be achieved without transfer of cells into a larger device as the cell population for any given culture increases. The applicant's earlier application (PCT/GB2016/051451) describes a cell culture container in which the wall element, being composed of a flexible material, is compressible with respect to its top and base sections.

The applicant now provides herewith an improved version of that earlier container which combines the advantages of the cell culture container of the earlier application (i.e. avoiding the requirement for constant passaging of cells into fresh culture devices, holding vessels, tubes etc.) with the advantages conferred by having individually configurable storage or culture devices. The improved device permits a variety of functions to be performed within a single container such as a cell culture container, as will be explained in more detail herein.

Accordingly the invention provides a device for use in growing, culturing and/or modifying cells, the device comprising a primary container such as a cell culture container, the primary container having a base section, a top section arranged substantially in parallel with the base section and a wall element arranged between the top section and the base section and defining an internal lumen of the primary container, in which the primary container has at least one optionally sealable inlet; and wherein the device further comprises one or more auxiliary containers in fluid communication with the primary container.

The device may comprise a plurality of auxiliary containers. The one or more auxiliary containers or the plurality of auxiliary containers may be external to the primary container and in fluid communication with the primary container.

The wall element of the primary container may be compressible with respect to the top and base section. The wall element of the primary container may be composed of a flexible material. The primary container may thereby have a 'concertina' or 'bellows' arrangement, e.g. it may have one or more z-folds in the wall element. Alternatively the primary container may have a syringe arrangement allowing it to be re-filled or emptied.

As described herein the invention may comprise means for shutting off fluid communication to a completely compressed or empty container.

One or more of the auxiliary containers may be detachably connected to the primary container, for example via the one or more sealable inlets. Accordingly one or more of the auxiliary containers may be configured such that they can be detached from the primary container and subsequently re-attached. This permits an auxiliary container thus configured to be filled with reagent and then attached or otherwise connected to the primary container. Any means of reversibly securing an auxiliary container to the primary container (such as a screw mechanism, or a push-fit lock) may be employed. Alternatively, the device may be manufactured so that the one or more auxiliary containers form a single closed interconnected system with the primary container. Filling of the one or more auxiliary containers with e.g. cell culture medium can then take place by introducing fluid via a separate port in each container. This separate port may be located in the top portion of an auxiliary container.

The device may comprise a plurality of auxiliary containers. The auxiliary containers may be independently in fluid communication with the primary container. Two or more auxiliary containers may be connected in parallel to the primary container rather than in series, i.e. in direct fluid communication with the primary container but not directly with one another. Additionally or alternatively, at least one auxiliary container may be in direct fluid communication with at least one other auxiliary container and may not be in direct fluid communication with the primary container. The auxiliary containers may be of varying sizes and volumes, depending on their configuration. One or more auxiliary containers may be in direct fluid communication with a further container such as a bioreactor. The present invention defines a means by which an auxiliary container originally in direct fluid communication with a first container, e.g. the primary container, may be brought into direct communication with a second container, e.g. a further container such as a bioreactor.

References throughout to a first container being in "direct" fluid communication with a second container mean that the contents of the first container may be transferred into the second container (or vice versa) without passing through an intermediate container.

Generally, one or more auxiliary containers will have a size and volume that is less than that of the primary container. However, it is envisaged that any auxiliary container configured to receive waste from the primary container will generally have a larger volume than the primary container.

One or more of the auxiliary containers may be located on the top section of the primary container.

Additionally, or alternatively, one or more auxiliary containers may be located at or near the base section of the primary container. Such a configuration may be used e.g. if it is intended to collect the product(s) of any reaction(s) carried out in the primary container. Such a configuration may be used e.g. if it is intended to carry out quality assessment or quality control of an ongoing process, e.g. a cell culture process, taking place in the primary container.

The invention also provides an auxiliary container for use with the device of the invention.

An auxiliary container of the invention may have the same general configuration as the primary container, i.e. it may comprise a base section, a top section arranged substantially in parallel with the base section and a wall element arranged between the top section and the base section and defining an internal lumen of the auxiliary container, in which the container has at least one optionally sealable inlet. The wall element of the auxiliary container may be compressible with respect to the top and base section. The wall element of the auxiliary container may be composed of a flexible material. The auxiliary container may thereby have a 'concertina' or 'bellows' arrangement, e.g. it may have one or more z-folds in the wall element. Alternatively the auxiliary container may have a syringe arrangement allowing it to be re-filled or emptied. It will be understood that it is necessary to be able to transfer the contents of an auxiliary container of the invention into another container and this can be achieved either by collapsing the auxiliary container or by inclusion of a syringe arrangement, as detailed herein.

An auxiliary container of the invention may comprise insulation means, such as a thermal sleeve, which is configured to maintain the contents of that auxiliary container at a particular temperature. Accordingly, an auxiliary container may be configured to maintain its contents at an optimal cell culture temperature (37 degrees Celsius), or room temperature (22 degrees Celsius), or refrigerated (e.g. around 4 degrees Celsius), or below freezing (e.g. around minus 4 degrees Celsius or lower, such as minus 20 degrees Celsius, or minus 80 degrees). Depending on its intended configuration, a device of the invention may have one or more auxiliary containers configured to maintain a variety of temperatures.

An auxiliary container of the invention may have a single outlet where it is configured to be attached in fluid communication with the primary container of the invention. Alternatively, an auxiliary container of the invention may have more than one outlet, e.g. two outlets on opposite sides. This arrangement permits one or more auxiliary containers to be connected in series.

Since the auxiliary container of the invention may be detachable from the primary container of the device of the invention, the present invention provides a kit of parts for assembly into a device of the invention, the kit comprising a primary container of the invention as defined herein together with one or more auxiliary containers as defined herein.

It will be understood that such the presently-defined arrangement of the device of the invention, which comprises one or more auxiliary containers in fluid communication with the primary container, allows a number of separate reactions to be carried out within a single container. In particular, multi-step cell culture within a device of the invention is envisaged. In addition, it will be understood that the device of the invention can be used for a series of treatments, e.g. exposing cells to a series of antibodies or small molecules. The device could also be used to purify a specific subpopulation of cells, e.g. from a biopsy.

Accordingly, where the device of the invention comprises a plurality of auxiliary containers, the auxiliary containers may be configured to contain different elements. In one example, a first auxiliary container may be configured to contain a cell culture medium, while another may be configured to contain a viral vector, another may be configured to contain a washing buffer, and yet further auxiliary containers may be configured to contain magnetic beads, growth factors, etc. Other configurations are possible, as can be readily envisaged by one of skill in the relevant art.

The device of the invention may be configured such that the primary container may be centrifuged or otherwise spun, e.g. on its central axis.

Accordingly the device of the invention may comprise additional apparatus such as a centrifuge or other means by which the contents of a container may be spun in order to separate out its contents. The device may comprise a rocking means for maintaining a rocking motion of a container; and/or may comprise a platform which can be vibrated to permit a container stationed thereon to be thus agitated. The device may comprise a means such as a lever, a plunger or a series of levers, plungers or bellows configured to compress the primary container and/or the one or more auxiliary containers. It will be understood that any such means should preferably be capable not merely of compressing or collapsing a container of the invention but also of re-opening it where this is required. Re-suspension of sedimented/pelleted cells e.g. following centrifugation might be effected by repeated compression/extension of the container to thereby agitate the medium. The device may comprise additional means such as sensor means, optical fiber, a gas supply for oxygen or other gases, a heating/cooling means and temperature control means, etc. Thus the device may be configured to maintain the primary container, and any optional further container(s) such as a bioreactor (as defined herein), at a particular temperature. This temperature will generally be an optimal cell culture temperature (37 degrees Celsius), or room temperature (22 degrees Celsius), but it may in some instances be lower, either for refrigeration (e.g. around 4 degrees Celsius) or freezing (e.g. around minus 4 degrees Celsius or lower, such as minus 20 degrees Celsius) of the cell culture; or even minus 80 degrees Celsius, where cryopreservation is required. The device may also comprise a magnet, which may be controllable between an on and off configuration. Such a magnet may be used in conjunction with an auxiliary container configured to hold metal beads, as described in more detail herein.

It will be understood that the conditions, such as the temperature of the primary container (and any optional further container(s) such as a bioreactor), can be maintained independently of the conditions within any of the one or more auxiliary containers which are in fluid communication with the primary container.

As detailed herein, a container of the invention (i.e. a primary container, auxiliary container and/or further container such as a bioreactor, each of which is defined in more detail herein) may have the same general configuration as the primary container, i.e. it may comprise a base section, a top section arranged substantially in parallel with the base section and a wall element arranged between the top section and the base section and defining an internal lumen of the container, in which the container has at least one optionally sealable inlet. The wall element of the container may be compressible with respect to the top and base section. The wall element of the container may be composed of a flexible material. The container may thereby have a 'concertina' or 'bellows' arrangement, e.g. it may have one or more z-folds in the wall element. Alternatively the container may have a syringe arrangement allowing it to be re-filled or emptied. Transfer of the contents of a container of the invention into another container may be achieved either by collapsing the container or by inclusion of a syringe arrangement, as detailed herein.

A container of the invention may be adjustable and may adopt a number of different configurations. It may be compressed from an expanded or partly expanded state or expanded from a compressed or partly compressed state. The different configurations may be achieved passively or actively, e.g. manually or under the control of an actuating device, such as a lever or plunger, as explained herein. The actuating device may operate in a reversible manner so as to cause the compression or expansion of a container of the invention as desired or required.

A container of the invention may be compressible from an open arrangement in which it is fully extended, through semi-open or semi-closed arrangements, in which it is partly compressed or collapsed, to a fully collapsed or compressed arrangement.

A container of the invention may be compressible with respect to the top and base sections where the wall element is deformable. The compression of a container of the invention may be analogous to that of a concertina or bellows, i.e. where the wall sections of the container are deformable and may be folded e.g. into z-folds. The top section and base section may be brought closer together by the deformation of the wall element. The deformation may occur along lines or zones of greater flexibility in the flexible material of the container. Alternatively, a container of the invention may have an arrangement analogous to a syringe, having an element that is moveable to either expel fluid from the container of the invention or draw it back in.

The compression of a container of the invention may therefore also be described as being along an axis tangential to the plane of the top section and the base section. Thus if the top section and the base section are arranged in substantially horizontal positions (where the container can be described as being in an upright configuration) the compression of the container occurs in a vertical sense. Likewise, if the top section and base section are arranged in substantially vertical positions (where the container can be described as being in a transverse or lateral configuration) the compression of the container occurs in a horizontal sense.

In the fully extended or open arrangement, a container of the invention may have a maximum available volume for culture of cells. In the fully collapsed or compressed arrangement a container of the invention may have a minimum available volume which is more suitable for storage or transport of the container, or as part of a step in processing cells by washing or pelleting cells. A container of the invention may be compressed by means of an actuating device which brings the top section and base section closer together. Likewise, a container of the invention may be expanded by means of an actuating device which moves the top section and base section further apart. It may be the same actuating device which achieves both compression and expansion. The device of the invention may therefore comprise one or more actuating devices for effecting relative movement of the top and base sections of a container of the invention.

Where a container of the invention is expanded from a closed or semi-closed arrangement, the expansion can be suitably controlled, e.g. by means of manual expansion of the container, or a mechanical expansion where the container is held within an actuating device that expands the container by moving the top section and the base section further apart. A container of the invention may also be capable of self-expansion in some embodiments where the container is fabricated from a suitable material. A container of the invention may also be expanded by means of introducing a fluid such as a liquid or a gas. Likewise a container of the invention may also be compressed by means of removing a fluid such as a liquid or a gas.

It will further be understood that the configuration of the device of the invention, with one or more auxiliary containers arranged in fluid communication with the primary container, allows for multi-step cell culture within a single container. Thus, the reaction may be initiated, following which the mixture may be centrifuged or otherwise spun to retain the cells of interest in the primary container, with the reaction medium being ejected into a suitably configured auxiliary container as waste upon compression of the primary container. Subsequently, the cells of interest may be resuspended in a further reaction medium which may be introduced into the primary container from a further auxiliary container. The centrifugation/spinning and resuspension sequence may be repeated as often as required in order to obtain a cell culture or cell culture product of interest. Other steps, such as introduction of a vector, or a label, or a selection medium, from further auxiliary containers, may be carried out as required with such steps including the presence of a suitably configured auxiliary container in fluid communication with the primary container. At suitable points, the medium may be ejected into a designated waste auxiliary container to permit reintroduction of fresh medium.

It will be understood that solid-liquid separation can be achieved by means other than centrifugation; thus, methods of gravity settling, standing wave or filtration means are also encompassed. Acoustic wave means of holding particles in suspension are well known, as set out e.g. in Chen et al. (2014) Lab Chip. March 7:14(5):924-30.

The invention accordingly provides a multi-step method of growing, culturing and/or modifying cells within a device of the invention. The method may comprise filling one or more auxiliary containers which are in fluid communication with the primary container of the invention with various reagents. Alternatively, one or more pre-filled auxiliary containers may be provided. The method may include connecting one or more pre-filled auxiliary containers to the primary container so as to be in fluid communication with the primary container. The reagents may include any reagents which are used in methods of growing, culturing and/or modifying cells. Accordingly one or more auxiliary containers may contain buffer, culture medium, pH stabilisers, plasmids, viral vectors, other vectors, growth factors, washing medium, labelled antibodies, other labelling moieties including magnetic beads, etc.

The method includes introducing cells of interest into the primary container and sequentially adding one or more of the reagents from one or more auxiliary containers into the primary container in order to effect the desired growth, culturing and/or modification of the cells. The method may also include one or more steps of carrying out certain processes in one or more of the auxiliary containers, whereby some or all of the cells within the primary container are moved into the requisite auxiliary container. Following completion of that step, the cells may then be transferred back into the primary container. The method may include a step of collecting cells or cell culture product into one or more auxiliary containers; and may include a step of freezing the collected cells or cell culture product. The method may include a step of sampling the collected cells or cell culture product, e.g. for quality control or other monitoring purposes. The method may include a step of transferring spent medium from the primary container into a suitably configured waste auxiliary container. The method may include a step of separating the cells out from the medium, which may be a centrifugation or spinning step. The cells may be separated out onto the base plate of the primary container or they may be separated out so that they attach to the walls of the primary container. The method may include a step of washing the cells. The washing step may take place following centrifugation or separation of the cells. Separation may be by means of filtration, spinning, gravity settling, or other known means. Alternatively the method may include a step of holding the cells in place for washing, e.g. via standing wave or acoustic wave means. The method may include a step of introducing a vector into the primary container. The method may include a step of introducing a label into the primary container. The method may include a step of introducing a selection medium into the primary container. The method may include a step of resuspending the cells in fresh medium. The method may include the electroporation of cells or transfection with lipid or chemical based reagents. The method may include the treatment of transfectants pools with antibiotics, auxotroph removal or any other means for selection. The method may include the exposure of cells to virus-like particles. The method may include density centrifugation to isolate cells based on size. The method may include a step of affinity purification. The method may include fed batch, perfusion or chemostat modes of bioreactor operation. The method may include aggregation of cells. The method may include the dissociation of cells from materials or from one another.

The method may include a step of transferring the cells from the primary container to a further container such as a bioreactor. The transferring may take place once the cells have reached a certain density (such as optical density) within the primary container. The method may include a step of culturing the cells within the further container. The method may include a step of transferring the cells from a first further container to a second further container, e.g. once the cells have reached a certain density (such as optical density) within the first further container. The method may include a step of connecting one or more auxiliary containers in fluid communication with the primary container such that they are in fluid communication with the further container(s), e.g. by means of a locking valve mechanism as defined in more detail herein. The method may include a step of connecting one or more auxiliary containers directly to a further container.

The method may include a step of regulating the temperature within any of the one or more auxiliary containers, the primary container, and/or the one or more further containers. Possible temperatures or temperature ranges are as defined herein. The method may include maintaining conditions (such as pH or temperature) within the primary container or further containers independently of the conditions within one or more of the auxiliary containers.

Any of the above steps may be carried out more than once, as required in order to effect the desired outcome.

The method may effect transfer of the contents of an auxiliary container via compression/collapse of the auxiliary containers, which may be a partial or complete collapse. Transfer may be effected via a syringe mechanism in the auxiliary container. The method may effect transfer of the contents of the primary container via compression/collapse of the auxiliary containers, which may be a partial or complete collapse. Transfer may be effected via a syringe mechanism in the primary container.

Thus the method may include the step of conducting initial modification of the cells within the primary container and/or one or more auxiliary containers, followed by completely collapsing the primary container into a further container such as a bioreactor. Prior to this step, the further container might be in a completely collapsed state.

It will further be understood that the primary container may be compressible in two directions: towards its base section, or towards its top section. Accordingly, if the primary container is centrifuged such that the cells of interest are pelleted out and rest on the base section of the primary container, it may be desirable to have an auxiliary container which is configured to hold the waste positioned in fluid communication with the top section of the primary container; and to compress the primary container towards its top section such that the waste fluid is ejected with minimal disturbance of the centrifuged pellets at the base section of the primary container. Conversely, if it is desired to collect the centrifuged product, it may be desirable to have an auxiliary container which is configured to receive that product positioned in fluid communication at or near the base section of the primary container and to compress the primary container towards its base section, thereby jettisoning the centrifuged product into the respective auxiliary container. It will be understood that the same arrangement may exist for any further containers such as bioreactors.

One or more containers may be connected in series. For example, the device of the invention may comprise an auxiliary container which is in fluid communication with a further auxiliary container, wherein the further auxiliary container is not in direct fluid communication with the primary container of the device. Additionally or alternatively, the device of the invention may further comprise one or more further containers, such as a bioreactor, in direct fluid communication with the primary container but not necessarily with the one or more auxiliary container(s). Thus, once the cell reaction is completed within the primary container, the cell medium may be ejected into a further container such as a bioreactor for further culturing. Ejection into the further container such as a bioreactor may be dependent on reaching a certain cell density, e.g. when optical density (OD) within the primary container reaches a certain predetermined level. The device of the invention may comprise a series of such bioreactors, of successively greater internal volume, with the cell culture being ejected into each subsequent bioreactor upon reaching a certain cell density.

Such further container(s) may be configured in the same manner as the primary container defined herein, e.g., to be compressible, and thereby save space by being compressed when not in use.

The primary container, the one or more auxiliary containers and the one or more further containers may have a means, such as a valve, which permits fluid communication through an outlet to be controlled. The valve or other means may be unidirectional, e.g., permitting the contents of an auxiliary container to be ejected into the primary container when the auxiliary container is compressed, but not vice versa. Alternatively, the valve or other means may be unidirectional in the other direction, e.g., permitting the contents of the primary container to be ejected into an auxiliary container when the primary container is compressed. Thus, one or more of the auxiliary containers may be configured to hold waste from the reaction, permitting several stages of a reaction to be performed within the primary container, with waste from each stage being transferred to a suitably configured auxiliary container. Alternatively, a valve may be bidirectional. Depending on its intended configuration, a device of the invention may have auxiliary containers with a mixture of bidirectional and unidirectional valves or other fluid control means.

The primary container, the one or more auxiliary containers and the one or more further containers may have an outlet and a fluid control means, such as a valve, on opposing sides of the container: by way of example, a container of the invention may have a means such as a valve in both its top section and its base section. This may permit one or more of the primary container, auxiliary containers, or further containers, or any combination thereof, to be connected in series. The valve or other means in the two opposed sides of the container may be configured to interact by forming a channel when the container of the invention is fully compressed. The channel may thereby assist in transfer of the contents of a container of the invention into a subsequent container. The valve or other means in the two opposed sides may be configured to interlock. Accordingly, where it is intended to use a container of the invention only once, the locking of the channel minimises dead space in the used container by shutting off fluid communication into that container. This may be important if there are any residues within the used container which might potentially contaminate the subsequent container if washed into it.

For example, once the primary container of the invention is emptied into a further container such as a bioreactor, it may be desirable to introduce reagents from an auxiliary container into the further container. Complete compression of the primary container may allow for any valve or other means in an auxiliary container which is in fluid communication with the primary container to interlock with a like valve or other means in the further container, thereby avoiding any reagent entering the dead space within the compressed primary container. In such a manner an auxiliary container may be placed into direct fluid communication with the further container. Additionally, or alternatively, it is envisaged that one or more auxiliary containers may be connected directly to a further container such as a bioreactor.

The wall element of a container of the invention (by which is meant the primary container, an auxiliary container or a further container such as a bioreactor, as defined herein) may comprise a plurality of lateral rigid sections in the wall arranged in parallel with the base section where each pair of lateral rigid sections is interleaved with a deformable region. The wall element of a container of the invention may comprise a rigid helical coil region having a deformable region provided either side of the helical coil region.

The top section, the base section and wall element of a container of the invention may form a bag which can be held within an external adjustable frame, or in which the bag comprises an internal adjustable frame within the material of the bag. Accordingly, one or more of the auxiliary containers in fluid communication with a container of the invention (e.g. with a primary container or a further container such as a bioreactor) may form a bag, which can be held within an external adjustable frame, or in which the bag comprises an internal adjustable frame within the material of the bag. Such a bag may be configured to act e.g. as an intravenous drip bag. It will therefore be understood the product(s) of any reaction(s) carried out in a primary container or further container may be directly collected into the bag, which can then be removed and transferred to an intravenous drip. Alternatively, the product(s) of any reaction(s) can be directly delivered to a patient from one of the lumens of the container, where the container is subdivided as set out herein.

As set out in the applicant's earlier application (PCT/GB2016/051451), a container such as the primary container may comprise a single internal lumen comprising a single chamber, or it may be divided by one or more closure means so as to form a plurality of sequentially arranged internal chambers within the internal lumen. In this way, the primary container can accommodate a number of different zones or regions in which different processes can occur either sequentially and/or in parallel when the primary container is in use. The plurality of chambers within a single closed-container system enables the simultaneous processing of multiple cell types each within their own chamber, with mixing only occurring if and when required. The primary container can be adjusted to provide such different chambers by selective opening and closing of regions in the container as described herein. Where the primary container comprises a plurality of lateral rigid sections the movement of the individual sections can be independently controlled thus permitting one or more pairs of sections to be opened while others remain closed. Each pair of lateral rigid sections may define an individual segment in the primary container. The primary container may therefore comprise several regions made up of one or more segments. The ability to open or close different segments or regions defining several segments selectively is an advantage of this aspect of the invention. The top section and/or base section and/or wall elements may have inlet and/or outlet ports. In this manner, the primary container can be used to process cells by moving the cells through the device by selectively opening and closing different segments or regions. The action of selectively opening or closing different segments or regions enables the volume and available surface area to be increased or decreased as desired according to the process being undertaken. The action of opening a segment or region may cause cells in culture to be moved from one chamber to another within the lumen of the container, or the cells in culture may also be mixed (e.g. after centrifugation). Cells can be moved in any direction depending upon the phase of the segments i.e. open or closed. Likewise the action of closing a segment or region may cause movement of cells and/or mixing. Full compression of the primary container may cause the cells in culture to be expelled from the container. Opening of the primary container from a closed arrangement when attached to or adjacent to a source of cells or liquid may cause liquid or cells to be drawn up into the lumen of the container where the container is suitably modified to receive such material or liquid via a cannula.

It will be understood that this previously-described arrangement may be applied to a container of the invention, whether a primary container, auxiliary container or further container such as a bioreactor.

The applicant's earlier application (PCT/GB2016/051451) also describes that a plurality of lumens may be formed by the action of heat-sealing across a suitable locus around the wall of a container such as the primary container thus annealing the walls of the container to form a seal. Such sealing may permit the selective removal of a part of a primary container containing cells or medium for storage (i.e. cryopreservation) and/or transport and/or waste removal (spent media) and/or cell selection.

It will be understood that this previously-described arrangement may be applied to a container of the invention, whether a primary container, auxiliary container or further container such as a bioreactor. However, the present invention provides selective removal which may be effected by compression of a container such as the primary container and subsequent ejection of the fraction of interest into one or more suitably configured auxiliary container(s). The one or more suitably configured auxiliary container(s) may then be detached. Optionally, one or more further auxiliary containers may subsequently be attached in order to collect further product.

The applicant's earlier application (PCT/GB2016/051451) also describes that a container such as the primary container may comprise a plurality of chambers disposed within the lumen of the primary container along the axis of the primary container perpendicular to the orientation of the base section and the top section. The plurality of chambers may have different widths, i.e. the chambers may be evenly or unevenly sized. The chambers may each independently be in fluid communication, or alternatively the chambers may each independently be in re-sealable fluid communication. Thus one or more chambers may be selectively isolated from one or more other chambers. Having chambers of different volumes within the single device enables a range of operations to be carried out that require either a specific cell or reagent density. For example, transfection and electroporation both require a high density of cells in a low volume; and inoculation requires a low density of cells in a large volume. Likewise for expensive reagents that need to be at a specific concentration to work efficiently, smaller volume chambers with higher cell density are more cost efficient. In such embodiments, a population of cells can be introduced through the top section of the primary container and subjected to processing in a first chamber, followed by selective closing of the first chamber and the selective opening of an adjacent second chamber coterminous with the closing of the first chamber thereby moving the cells into the second chamber for subsequent processing. For example, the first chamber may be used to transfect the cells where the first chamber has a relatively small available volume and the second chamber may have a greater available volume for culture and expansion of the transfected cells, whereby additional culture medium can be supplied if required. More chambers can therefore be formed as necessary according to the processing method to be adopted where the overall dimensions of the container can be chosen accordingly.

It will be understood that this arrangement may be applied to a container of the invention, whether a primary container, auxiliary container or further container such as a bioreactor. In the alternative, as set out in more detail herein with reference to the Figures, one or more auxiliary containers may be in fluid communication with the primary container, or a further container such as a bioreactor, by means of a corrugated tube. The tube may be compressible in the same direction as the container it extends into and thus not interfere with compression or collapse of that container. The tube may have a port at the end distal from the end which may be in fluid communication with the auxiliary container and thus permit the contents of the auxiliary container to be ejected into a precise location within the primary or further container. Additionally or alternatively, the arrangement permits the contents of the primary or further container to be ejected into an auxiliary container from a precise location within the primary or further container. It will be understood that placement of the port on the tube will determine the location within the primary or further container where the transfer of contents will occur.

A container of the invention may be composed of the same flexible material throughout. However, the top section and/or the base section may be composed of material which is different from that of the wall element. The material used in the top section and the base section may be less flexible than that of the wall element since in use it is not required to be compressed or expanded. The material may be a rigid material so that these sections have more structural rigidity. The top section may be composed of a different material from that of the base section. For example, the base section of a container of the invention may be a gas permeable membrane as defined below. This is particularly envisaged for the primary container and any further container such as a bioreactor. Alternatively, all parts of a container of the invention may be composed of the same flexible material.

The top section and/or the base section of a container of the invention may be composed at least in part of a metal such as stainless steel or the like where metal is required to produce an electroporation effect within the container. Alternatively, any generally suitable plastic material for use in cell culture, processing and storage (e.g. cryopreservation), such as polyethylene (high-density or low-density polyethylene HDPE or LDPE), polyvinylchloride (PVC), polypropylene (PP), polystyrene (PS) including high impact polystyrene, polyamides (PA), acrylonitrile butadiene styrene (ABS), polycarbonate (PC), polycarbonate/acrylonitrile butadiene styrene (PC/ABS) etc. may be used.

The flexible material may be a gas permeable material and it is envisaged that the base section of a container (such as the primary container or a further container such as a bioreactor) of the invention may be made up of such a material. The flexible material may be a plastic material. The flexible material may be a polyethylene (optionally a low-density polyethylene (LDPE)), cis-1,4-polybutadiene, a methacrylate such as poly (ethyl methacrylate), a phthalate such as poly (ethylene terephthalate), poly (vinylidene chloride), a cellulose acetate such as cellulose acetate butyrate, a silicone, flouroethylenepolypropylene, polyolefin, or ethylene vinyl acetate copolymer.

A container of the invention may be suitable for cell culture and processing of cells, including the use of the container in cell therapy, gene therapy vector production and/or exosome production. A container of the invention may be suitably sterilised prior to use (e.g. by gamma irradiation or other means). Optionally the internal surface of the device may be coated with or comprise biologically active agents which can act on the cells in culture and/or induce differentiation.

A container of the invention may comprise an outlet, as defined herein, for example in its base section, where each outlet and any inlet may be adapted for connection to a connector, for connection to one or more further container(s) of the invention, or fitted with an adjustable or removable closure means, or a removable microporous filter. The base section of a container of the invention may comprise a collection region. The base section of a container of the invention may be substantially planar (horizontal) or it may be configured to be angular in cross-section, for example it may have a collection region to collect cells through settling in the device.

Where a container of the invention has a plurality of lateral rigid sections as defined herein, there may be of from 2 to 3, 2 to 4, 2 to 5, 2 to 6, 2 to 7, 2 to 8, 2 to 9, or 2 to 10, sections or more. The number of lateral rigid sections may be 2, 3, 4, 5, 6, 7, 8, 9, 10, or greater. In some embodiments the number of lateral rigid sections may from 10, 20, 30, 40, 50, 60, 70, 80, 90 or 100, or greater. The minimum number of lateral rigid sections in such an embodiment is 2 in which the top section comprises a lateral rigid section and the base section comprises a lateral rigid section with a deformable region interposed between. The lateral rigid sections may be composed of a reinforced section of material compared to the deformable regions in the wall of the container, such as a wire frame.

A container of the invention may be of circular, square, rectangular, elliptical, or triangular cross section. Alternatively, a container of the invention may comprise a number of different sections or regions of a variety of cross sections, such as for example a series of circular cross sections with variable (increasing and/or decreasing) diameters.

A container of the invention may be adapted to permit partial occlusion between individual segments or sections/chambers within the lumen of the container whilst still permitting liquid flow between segments or sections/chambers. For example, the lumen of the container may comprise a plurality of connected chambers wherein each chamber may be composed of a series of segments formed from pairs of lateral rigid sections. The plurality of connected chambers can further be provided with a releasable closure means at either end of each the plurality of connected chambers. The closure means may be a clamp. In other embodiments, the chambers can be permanently sealed using a heat sealer or similar to cause a welding of the wall element at a desired location so that an individual chamber (section) can be removed from the container.

A container of the invention can be provided with a membrane or filter located within the lumen at the deformable region to partition the lumen into a plurality of segments formed from pairs of lateral rigid sections. The membrane or filter can be perforated by one or more holes. The membrane or filter can semi-partition the lumen up to 35%, 40%, 45%, 50%, 55%, 60%, 65%, 70%, 75%, 80%, 85%, 90%, 95%, or 99% or 100% of the available surface cross-sectional area of the lumen. The membrane can be non-contiguous (i.e. the membrane does not wholly partition the lumen) with the wall element and thus form a series of baffles arranged within the internal lumen. For example, the baffle elements may be arranged at alternate lateral rigid sections or at each lateral rigid section. The material of the membrane or filter can be the same or different as the material forming the wall element. The membrane may be a cellulose, e.g. nitrocellulose membrane. The filter may be a microporous filter. The membrane or filter may be releasable.

A container of the invention may have a plurality of internal wall elements arranged concentrically within the lumen of the chamber. In this embodiment, the container may also be provided with series of concentric internal surfaces with decreasing cross-sectional area, but which do not absolutely partition the internal lumen. In such an embodiment, the container comprises a series of nested wall elements arranged concentrically with reducing cross sectional areas. However, liquid flow is possible around and throughout the internal lumen of the container in order to permit cells in culture to be attached to all available surfaces. The arrangement need not necessarily be circular and other regular geometric shapes are possible. The only requirement is that each smaller nested surface fits within the preceding larger nested surface up to the wall element of the container.

Each lateral rigid section may be of the same or different cross-sectional area as the deformable region. In this manner, the container may be composed of a series of interlinked chambers with increasing or decreasing volume and surface area.

The base section of a container of the invention may be frusto-conical in shape having a substantially planar horizontal base region. The base section may be configured to engage with a delivery mechanism for release of cells from the container, such as in a method of administration of cells to a subject as described herein. An outlet may therefore be provided in the base section also to permit such release or administration. Where an outlet is present, it may be adapted to accept a cannula, e.g. by means of a Luer lock connector ("Luer-Lok™"). The outlet may be sealable with an adjustable and/or removable closure means.

The top section of a container of the invention may be frusto-conical in shape. An inlet in the top section may be adapted to accept a cannula, e.g. by means of a Luer lock connector. The inlet in the top may be sealable with an adjustable and/or removable closure means, or provided with a removable microporous filter. The top section may be substantially planar (horizontal) or it may be configured to be angular in cross-section.

Any inlet and outlet may independently function in the reverse manner as required. References to a cannula include any type of needle used in delivery of cells or fluids to a subject, or used in obtaining samples of biological material or liquid from a subject. Where present, the cannula may be in fluid communication with the internal lumen of the container.

This aspect of the invention extends to a container of the invention comprising cells in culture and cell culture medium. The container comprising cells may be frozen.

In this aspect of the invention, cells may be cultured in the primary container of the invention and/or in one or more further containers such as a bioreactor. The cells may be in suspension culture or attached to a substrate. The substrate may be removably affixed to one more internal surfaces in the lumen of the container, or removably affixed to microparticles. The cells may be subjected to mixing, or centrifuging, followed by re-suspending in fresh medium, using auxiliary containers, as defined herein, to deliver the fresh medium and to hold any waste medium, as described in detail herein. The flexible material of the collapsible container (or a portion thereof) may be gas permeable which can enable gas transfer to supply gas, for example oxygen, to the cells.

In order to increase the scale of any given culture, the primary container may be extended from closed or semi-closed arrangement in which the primary container is collapsed in full or in part to an open or semi-open arrangement in which the primary container is extended. Alternatively, the device of the invention may further comprise one or more collapsible further containers such as bioreactors, which may each be of successively increasing volume. The cell culture may be transferred from one container to the next on reaching a certain density, such as optical density.

As can be seen, the device of the invention may have a variety of orientations and arrangements. It is suitable for multi-step processing of cells as described herein as well as for increasing scale of cell culture. The device may comprise a single (primary) container or a primary container and one or more further containers in which different processing steps may be carried out, suitably sequentially. It will be understood that the invention provides one or more auxiliary containers in fluid communication with the primary container. The one or more auxiliary containers may allow reagent to be delivered to a particular chamber within the primary container, and/or to a particular chamber within a further container. The one or more auxiliary containers may allow product/waste/etc. to be collected from a particular chamber of the primary container and/or from a particular chamber within a further container. Because the one or more auxiliary containers may be detachable from the primary container, it will be understood that this provides an easy way to collect product from the primary container, or maintain conditions within the primary container, whilst permitting a continuous cell culture process to run.

It will likewise be understood that because the one or more auxiliary containers may be individually regulated e.g. for temperature, pH, etc, this allows delivery or collection of their contents under the precise conditions required. Accordingly the one or more auxiliary containers may be configured for very different conditions from those within the primary container and any further containers such as bioreactors, without thereby contaminating or otherwise negatively affecting the conditions within the primary container.

The invention further provides a method for culturing cells in a primary container of the invention, and/or within a further container such as a bioreactor, as herein defined.

The method may further comprise one or more steps of washing, separating and/or cryopreserving the cells, with reagents (such as buffer, washing medium, additional medium, selective medium, plasmid, labels, antibodies, etc.) being delivered from one or more auxiliary containers in fluid communication with the primary container of the invention; and any waste or culture product (such as cells, protein, enzyme, antibody, etc.) being collected into one or more auxiliary containers in fluid communication with the primary container of the invention. The steps may take place in any appropriate order and be repeated as desired. Some steps may take place within one or more auxiliary containers in fluid communication with the primary container. For example, it may be desired to carry out some steps (such as transfection of cells) in a smaller volume of liquid. Accordingly, the method may include a step of transferring the medium from the primary container to one or more auxiliary containers for transfection, followed by a step of transferring the transfected cells back to the cell culture medium in the primary container. It will be understood that these steps may be carried out in one or more further containers such as bioreactors, with one or more auxiliary containers of the invention being delivering or collecting fluid to or from the further containers in a similar manner to that described for the primary container.

The method may additionally comprise centrifuging a container of the invention to form a pellet of cells; the supernatant liquid may then be displaced as described herein, e.g. by collapsing the container (by collapsing the container in the manner of closing an open concertina) optionally in an upwards direction and ejecting the supernatant into one or more auxiliary containers, followed by re-suspending the cell pellet, suitably by re-opening the container in the manner of opening a closed concertina, with additional culture medium or other suitable medium (such as a washing buffer) being delivered from one or more further auxiliary containers. The culture of cells in the collapsible container may be subjected to freezing (e.g. cryopreservation) for transport or storage, or further culturing, including optional activation steps or processing and subsequent administration to a subject. Administration to a subject may be from a bag as described herein, which may be configured for intravenous administration, e.g. as part of a drip device.

The culturing of the cells may include the step of transfection of the cells in order to introduce a heterologous nucleic acid (genetic material) into the cells which may be in the form of a nucleic acid sequence, optionally contained in a vector, which may encode a protein or RNA sequence of interest with accompanying regulatory and control elements with respect to gene expression such as a promoter. The nucleic acid sequence may be DNA or RNA. The step of transfecting the cells may suitably occur in a small volume of liquid, and thus the method may include a step of carrying out transfection in an auxiliary container which is in fluid communication with the primary container, or with a further container such as a bioreactor, as described herein.

Where a container of the invention comprises a number of discrete separate chambers within the lumen of the container, as described herein, the step of transfection can take place in a designated region of the chamber which may be arranged so as to hold a reduced volume of liquid in order to facilitate the transfection of the cells.

Different processing steps can be arranged to take place in different auxiliary containers which are in fluid communication with the primary container, or in fluid communication with a further container such as a bioreactor.

The device of the invention may be used to culture any prokaryotic or eukaryotic cell, suitably an animal cell, e.g. a mammalian, cell. The cells may be human or non-human. Examples of sources of suitable non-human cells include, rodents such as mice, rats, and guinea-pigs, as well as ungulate animals selected from ovine, caprine, porcine, bovine and/or equine species, or non-human primate species. However, the cells may be bacteria, yeast, fungi or plant cell in origin also.

The cells may be of any type including somatic cells and non-somatic cells. The cells may be stem cells derived from any stage of development of the embryo, foetus or adult animal. The cells may be genetically modified cells, such as chimeric antigen receptor T-cells (CARTs). The cells may be from a deposited cell line, such as genetically-modified Chinese Hamster Ovary (CHO) cells to produce recombinant proteins.

For example, embryonic stem (ES) cells, including cells of non-human origin. The cells may be derived from a deposited cell line, such as an ES cell line. The ES cells may be derived from means which do not necessitate the destruction of a human embryo such as parthenogenetic activation, as described in WO 2003/046141. The cells may be cells of a cancer or a hybridoma which can be caused to proliferate in culture and/or produce monoclonal antibodies. The cells may also be derived from the result of somatic cell nuclear transfer (SCNT) in which the nucleus of a somatic cell is placed into an enucleated oocyte.

The cells may be pluripotent stem cells, for example primate pluripotent stem (pPS) cells, for example human embryonic stem (hES) cells. Where the cells are stem cells, the source may be from any tissue of the body, including mesenchymal stem cells (including umbilical cord derived stem cells), neural stem cells or haematopoietic stem cells. Also included are induced pluripotent stem (iPS) cells.

Accordingly the invention also provides a method of treating a medical or veterinary condition in a subject comprising administering cells to the subject from a container of the invention, as defined herein.

The method of treatment of a medical or veterinary condition can include cell therapy by way of administration of cells, including genetically modified cells, to a subject in need thereof. Likewise a method of treatment of a medical or veterinary condition can include products produced by the cells including exosomes, conditioned media, monoclonal antibodies and recombinant proteins, to a subject in need thereof.

The cosmetic treatment can include any non-therapeutic method of treatment which provides a cosmetic (aesthetic) enhancement by way of administration of cells to a subject.

The cells may be cultured in a device according to the invention prior to administration, including optionally washing and re-suspending the cells in the container.

The device of the invention may optionally comprise a cryopreserved population of cells in a container of the invention which are subsequently thawed prior to administration. Suitably the thawed cells may be resuspended in a physiologically acceptable medium before use. The cells can be further washed, centrifuged and resuspended in the container again if required. The physiologically acceptable medium may be any generally acceptable buffer, adjuvant and/or diluent as required for the final formulation to be administered to the subject. For example, the medium may be phosphate buffered saline (PBS), suitably at pH 7.4.

The cells may be administered from a container, more preferably, from an auxiliary container of the invention, in the form of an injection. The container or the suitably configured auxiliary container may be provided with a cannula for administration of the cells, for example by means of a Luer lock connector. The container or the suitably configured auxiliary container may be provided with an actuator means for delivery of the cells. The actuator means may comprise a lever or other means providing a force to compress the container of the invention which can function as in the action of a syringe device. The actuator may be manually operated or operated controlled by an external electrical control system. The actuator means can therefore act as a compacting mechanism which acts to control the collapse of the container or the suitably configured auxiliary container to cause the exit of the cells from the container into the subject through the cannula.

The cells may also be administered by way of an infusion from a container, or more preferably, from an auxiliary container of the invention, in which the container or the suitably configured auxiliary container may be expanded to its greatest extent. In this embodiment, the cells may be suspended in a greater volume of medium as appropriate. The infusion may be administered passively, by a bidirectional linear actuator (e.g. syringe-driver-like device) operating under the control of an external electrical system may be provided as required or necessary for greater control.

The invention also provides a method of obtaining a biological sample from a subject comprising inserting a cannula into the subject in which the cannula is disposed within a container of the invention as defined herein, such as a suitably configured auxiliary container as defined herein. A base section of the container of the invention may be provided with the cannula, and the container of the invention may be composed of a flexible material, where said container is operatively connected to an actuator means for expanding the container thereby removing the sample from the subject.

The actuator means may be configured to open the container of the invention from a closed or semi-closed arrangement in order to permit ingress of the sample into the lumen of the container.

The actuator means may comprise a lever or other means providing a force which can expand the container as in the action of a syringe or other biopsy device. The actuator may be manually operated or operated controlled by an external electrical control system.

The cannula of the container may be inserted into to a blood vessel or bone marrow cavity. The container may be used to obtain cells, for example stem cells, from the subject such as blood, bone marrow, umbilical cord, adipose tissue, amniotic fluid etc. which can be conveniently biopsied in this manner. Where the container is a suitably configured auxiliary container, the sample may then be delivered from the container into a primary container of the invention by attaching the auxiliary container to the primary container so that it is in fluid communication therewith.

The present invention therefore provides for the processing of cells within a single device with multiple unit processes taking place as desired within the primary container via delivery/extraction of desired reagents, waste, cells, or product into or from one or more auxiliary containers in fluid communication with the primary container, thereby avoiding the risk of contamination. The system is simpler to use and further avoids the complexity of existing approaches. The invention provides for the safer processing of cells with improved reproducibility and ease of use.

The invention also provides for the extraction of cells from a patient (biopsy, such as blood or bone marrow), separation of cells, processing of cells (including cytokine stimulation and/or genetic modifications), solid-liquid separations and loading into a delivery device where the cells can be cultured in the same device throughout the entire process.

The invention will now be further described by way of reference to the following Examples and drawings which are present for the purposes of illustration only and are not to be construed as being limitations on the claimed invention. Reference is made to the following Figures also in which:

FIG. 1 shows a representation of one embodiment of the device of the invention in two separate arrangements. FIG. 1(a) shows a perspective view from the side of the device; and FIG. 1(b) shows a top view.

FIG. 2 shows a representation of the embodiment of FIG. 1 showing how a lever or plunger mechanism might expel medium from an auxiliary container into the primary container. FIG. 2(a) shows the lever or plunger ready to compress the auxiliary container; and FIG. 2(b) shows the auxiliary container in its fully closed form (fully collapsed).

FIG. 7 shows how temperature control can be varied across the containers of the invention. FIG. 7(a) shows an embodiment in which the primary container of the invention is maintained at the same temperature as the auxiliary containers; FIG. 7(b) shows that the auxiliary containers may be maintained at different temperatures from one another and from the primary container.

FIG. 8 shows various options in which cells may be cultured within a primary container or further container (such as a bioreactor) of the invention. FIG. 8(a) shows an embodiment in which the cells are present at the base of the container (possibly following centrifugation); FIG. 8(b) shows an embodiment in which cells are cultured at the base of individual chambers within the container; FIG. 8(c) shows an embodiment in which cells are maintained in a container while being spun; and FIG. 8(d) shows an embodiment in which cells are maintained in a container while being rocked from side to side.

Figure 9:
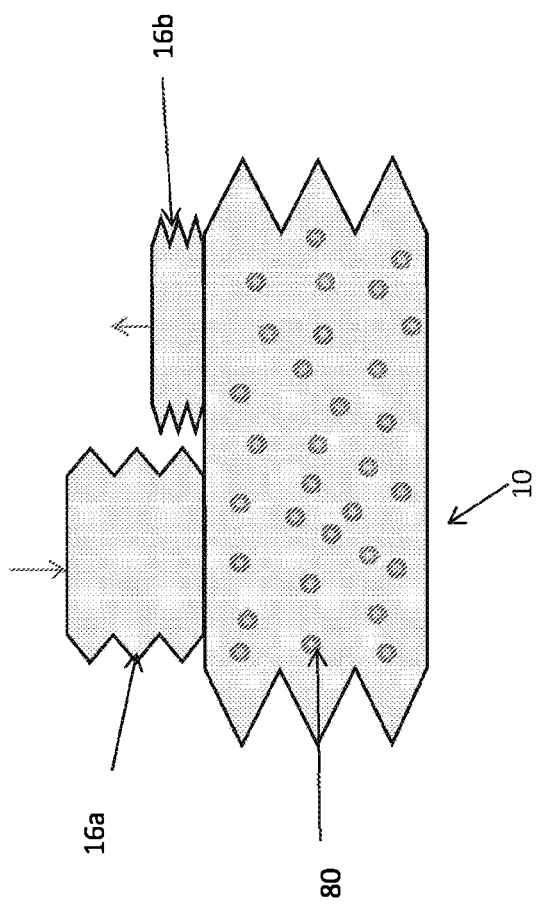

FIG. 9 shows how a plurality of auxiliary containers might work in conjunction with the primary container.

FIGS. 10a to 10(h) shows a multi-step process of culturing cells in a device of the invention.

FIG. 11 shows a valve arrangement in a compressible container of the invention. FIG. 11(a) shows the arrangement when the container is not fully closed. FIG. 11(b) shows the arrangement when the container is fully closed. FIG. 11(c) is a detail view of FIG. 11(b). FIG. 11(d) is a schematic showing how fluid communication can change as a result of the valve arrangement described herein.

FIG. 12 shows an arrangement whereby a container of the invention may have a removable base that is constructed of different material from the rest of the container.

Figure 13:
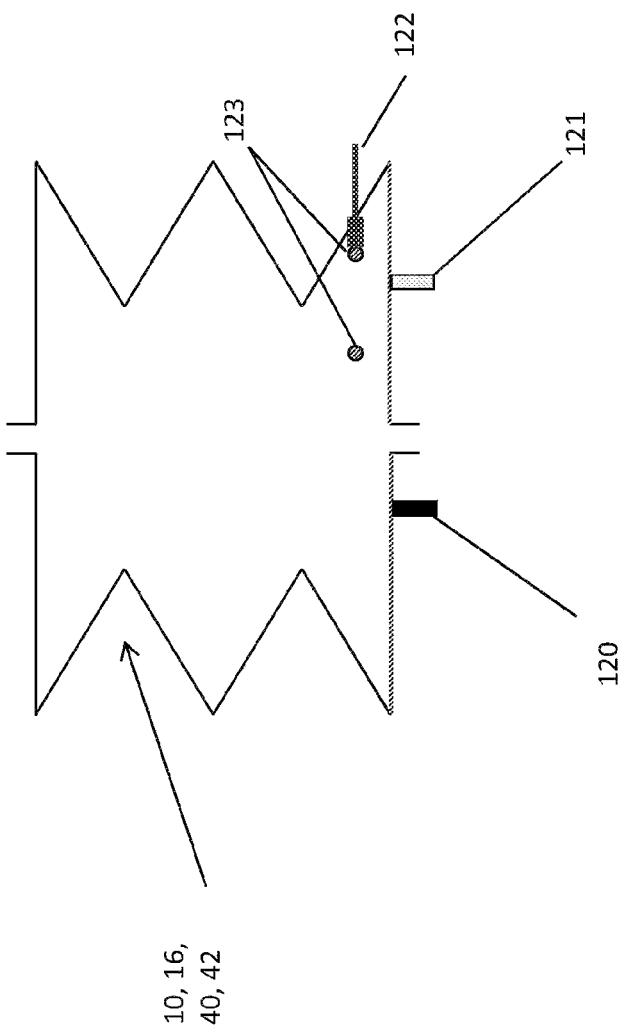

FIG. 13 shows examples of sensor options within a container of the invention.

FIG. 14 shows options for separation of cell and liquid. FIG. 14(a) shows a bucket centrifuge configuration, with cells pelleted out to land on the base of the container. FIG. 14(b) shows the results of a different centrifugation, where cells are spun out to attach to the wall of the container. FIG. 14(c) shows a collapsible container of the invention in an open state. FIG. 14(d) shows a collapsible container of the invention in a partially collapsed state.

FIG. 15 shows a configuration of the device where components may be removed or added at specific locations within a container. FIG. 15(a) shows how a configuration works with the cells spun and plated to the side walls of the container. FIG. 15(b) shows how a configuration works with the cells centrifuged to the base of the container.

FIG. 16 shows a configuration of the device for purification using magnetic beads. FIG. 16(a) shows the initial setup, with the magnet switched off and the magnetic beads held in an auxiliary container. FIG. 16(b) shows the configuration of 16(a) with the beads transferred from the auxiliary container into a container holding the cells. FIG. 16(c) shows the configuration once the magnet is switched on. FIG. 16(d) shows the configuration of FIG. 16(c) once the container holding the cells is emptied and the unbound cells are transferred to a further auxiliary container. FIG. 16(e) shows the configuration of FIG. 16(d) as the container holding the cells is refilled with dissociation buffer. FIG. 16(f) shows the configuration of FIG. 16(e) with the cells resuspended in a wash buffer. FIG. 16(g) shows the collection of target cells in a further auxiliary container.

Figure 17:
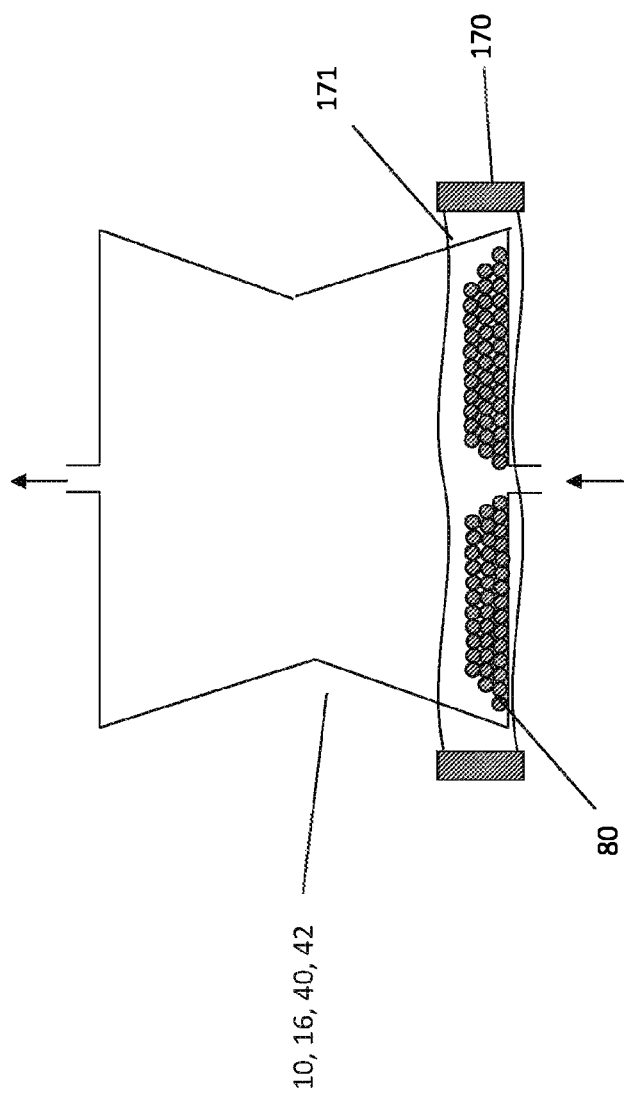

FIG. 17 shows a configuration where cells are held in place with acoustic wave technology while being washed within a container of the invention.

Figure 18:
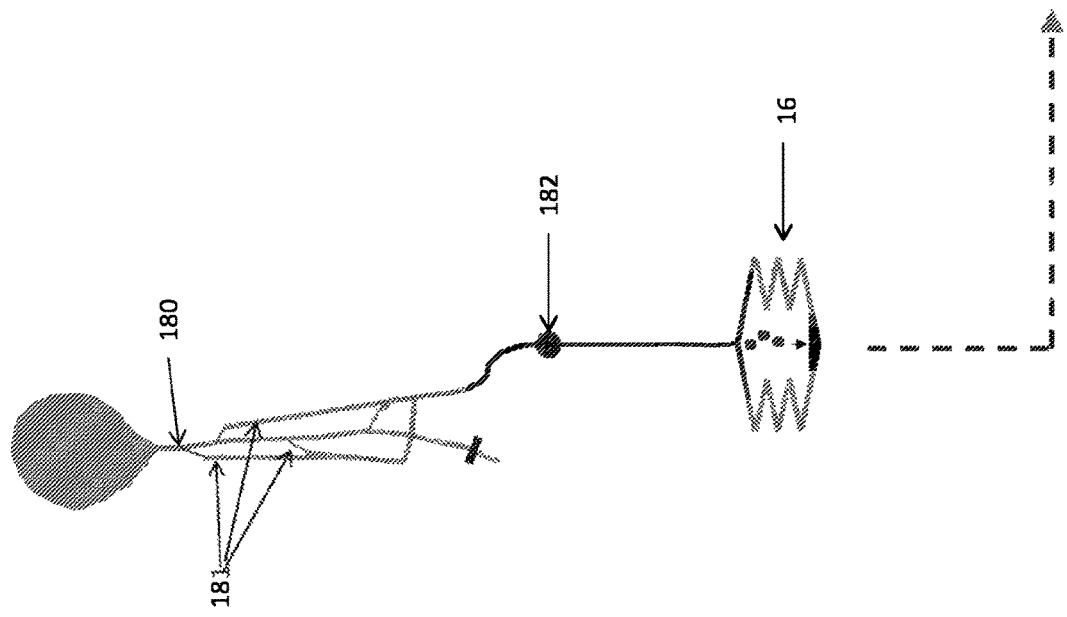

FIG. 18 shows a method of collecting blood within an auxiliary container of the invention for use in further processing.

FIG. 19 shows one configuration of a device of the invention for processing collected blood. FIG. 19(a) shows the transfer of blood from the auxiliary container into a main container for processing. FIG. 19(b) shows separation of the blood into vertical fractions via rotation of the main container. FIG. 19(c) shows the removal and collection of the plasma fraction into an auxiliary container by compression of the main container. FIG. 19(d) shows the removal and collection of the stem cell fraction into a further auxiliary container by compression of the main container. FIG. 19(e) shows the final product: three separate containers each having the separate fractions.

Figure 19B:
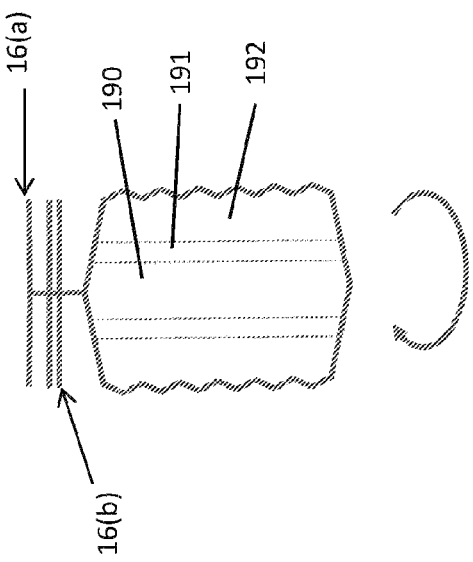
Figure 19A:
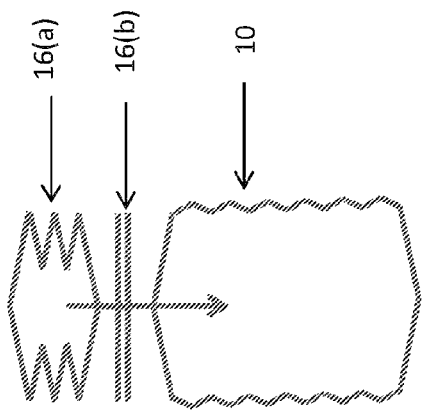
Figure 19E:
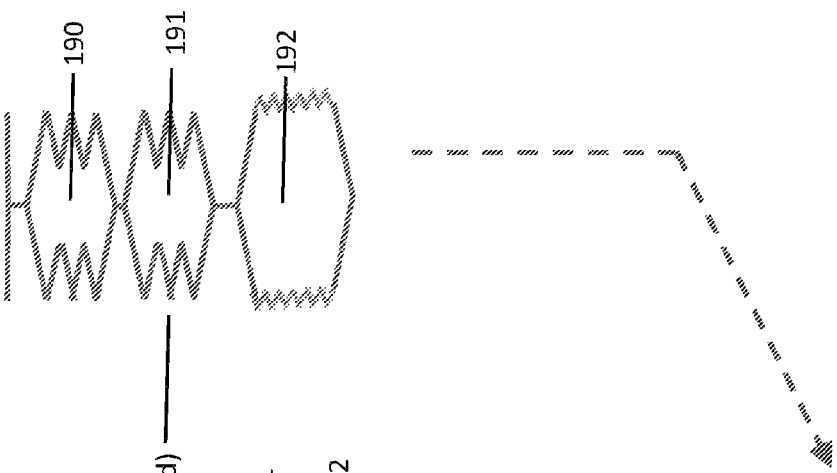
Figure 19D:
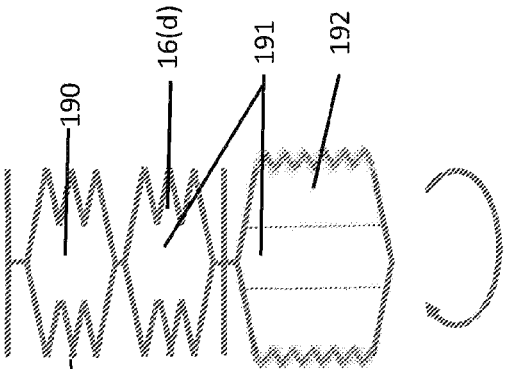
Figure 19C:
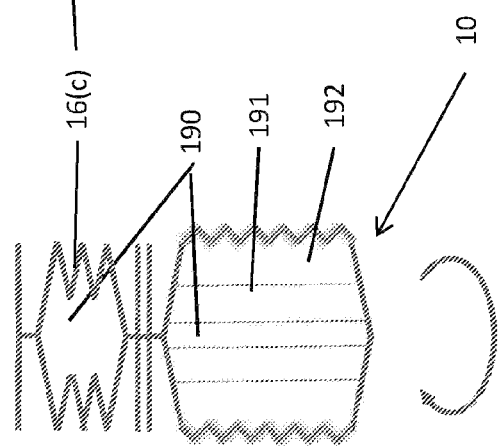
Figure 20A:
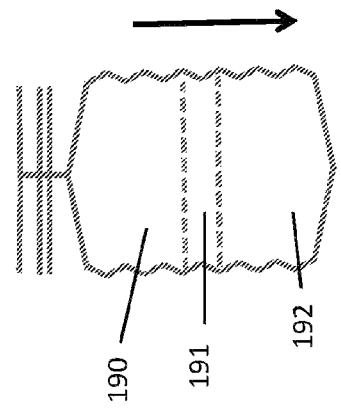
Figure 20B:
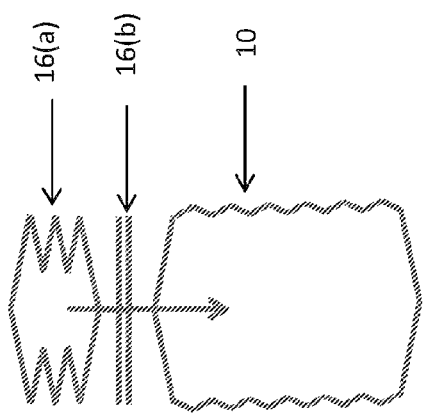

FIG. 20 shows a variant on the method shown in FIG. 19. FIG. 20(a) shows the transfer of blood from the auxiliary container into a main container for processing. FIG. 20(b) shows separation of the blood into horizontal fractions via centrifugation of the main container. FIG. 20(c) shows the removal and collection of the plasma fraction into an auxiliary container by compression of the main container. FIG. 20(d) shows the removal and collection of the stem cell fraction into a further auxiliary container by compression of the main container. FIG. 20(e) shows the final product: three separate containers each having the separate fractions.

FIG. 21 shows an alternative construction of the valve arrangement shown in FIG. 11, showing how fluid communication between a series of containers can be controlled using a single conical insert.

DETAILED DESCRIPTION OF THE FIGURES

FIG. 1 shows one embodiment of a device of the invention comprising a primary container (10) comprising a base section (12), a top section (14) and a wall element (8). The wall element (8) may comprise rigid sections laterally arranged in parallel with the base section (12). The figure shows the container in the upright configuration.

Each adjacent pair of intermediate rigid sections may be interleaved with a deformable region. The action of a compressive downward force perpendicular to the vertical axis of symmetry of the container causes the container to collapse to a partly closed arrangement and then to a fully closed arrangement.

The primary container (10) has at least one inlet (not shown) which may function as a removable closure means or temporary seal. To each inlet can be connected an auxiliary container (16) in fluid communication with the primary container (10). In FIG. 1(a) the auxiliary containers are arranged so that all are connected in parallel, i.e. each is in direct fluid communication with the primary container (10) but not with another auxiliary container (16). Each of the auxiliary containers (16) may have different configurations (16(a) to 16(e)). For example, one auxiliary container (16(a)) may be configured to contain a growth factor; another auxiliary container (16(b)) may be configured to contain a reprogramming vector; another auxiliary container (16(c)) may be configured to contain a wash buffer; another container (16(d)) may be configured to contain a medium; while another auxiliary container (16(e)) may be configured as a waste container. Thus, in this embodiment the various auxiliary containers (16) are of different configurations and may be of different sizes and volumes. The auxiliary containers (16) may be of a smaller size and volume from the primary container (10), although any waste auxiliary container(s) are likely to be of larger volume than the primary container.

As shown in FIG. 1(b) in this arrangement the auxiliary containers are connected via the top section (14) of the primary container (10). The primary container is circular in cross section. This circular cross section is not essential, but it has certain advantages in terms of e.g. spinning or centrifuging.

FIGS. 2(a) and 2(b) show the primary container (10) together with elements of a larger device (shown in part). This device may contain a centrifuge or other spinning device (not shown), as well as means (20,22) by which the primary container (10) and the auxiliary containers (16) may be compressed or uncompressed to effect transfer of their contents. An arm or other means (not shown) may move the means (20) which may be in the form of a lever or plunger so that it is able to compress the auxiliary container (16(a)). Preferably the same means (20) can also uncompress the auxiliary container. The contents of the auxiliary container (16(a)) are thus transferred to the primary container (10). Alternatively, the primary container (10) may be rotated upon a centrifuge or other spinning means (not shown) so that the means (20) is positioned above the auxiliary container (16(a)). The device (not shown) also contains a means (22) by which the primary container (10) may be compressed or uncompressed. In some configurations, the means (20) for compressing or uncompressing the auxiliary containers (16) and the means (22) for compressing or uncompressing the primary container (10) are the same thing, e.g. the lever or plunger may be moveable to act upon the primary container (10) as well as upon the auxiliary containers (16).

Figure 3:
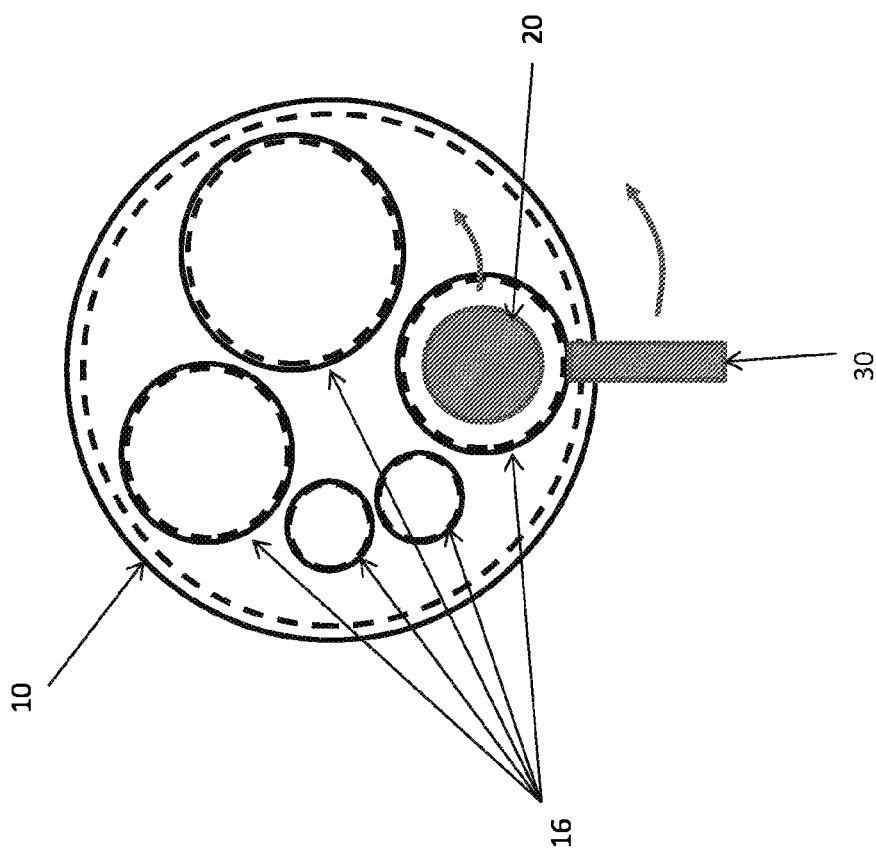
FIG. 3 shows a representation of the embodiment of FIG. 1, showing how a valve operator arm with a lever or plunger can move from one auxiliary container to the next, either via movement of the arm itself or via rotation of the primary container.

FIG. 3 shows the arrangements available to a device as shown in FIG. 2. Thus, the cell culture device may act to rotate the primary container (10) in the direction shown by the curved arrow. Additionally or alternatively, an arm (30) of the device may be connected to the means (20) for compressing or uncompressing the auxiliary containers (16). In such a configuration, the arm (30) of the device may move as shown by the arrow in order to move the compressing means (20) between the auxiliary containers (16).

Figure 4:
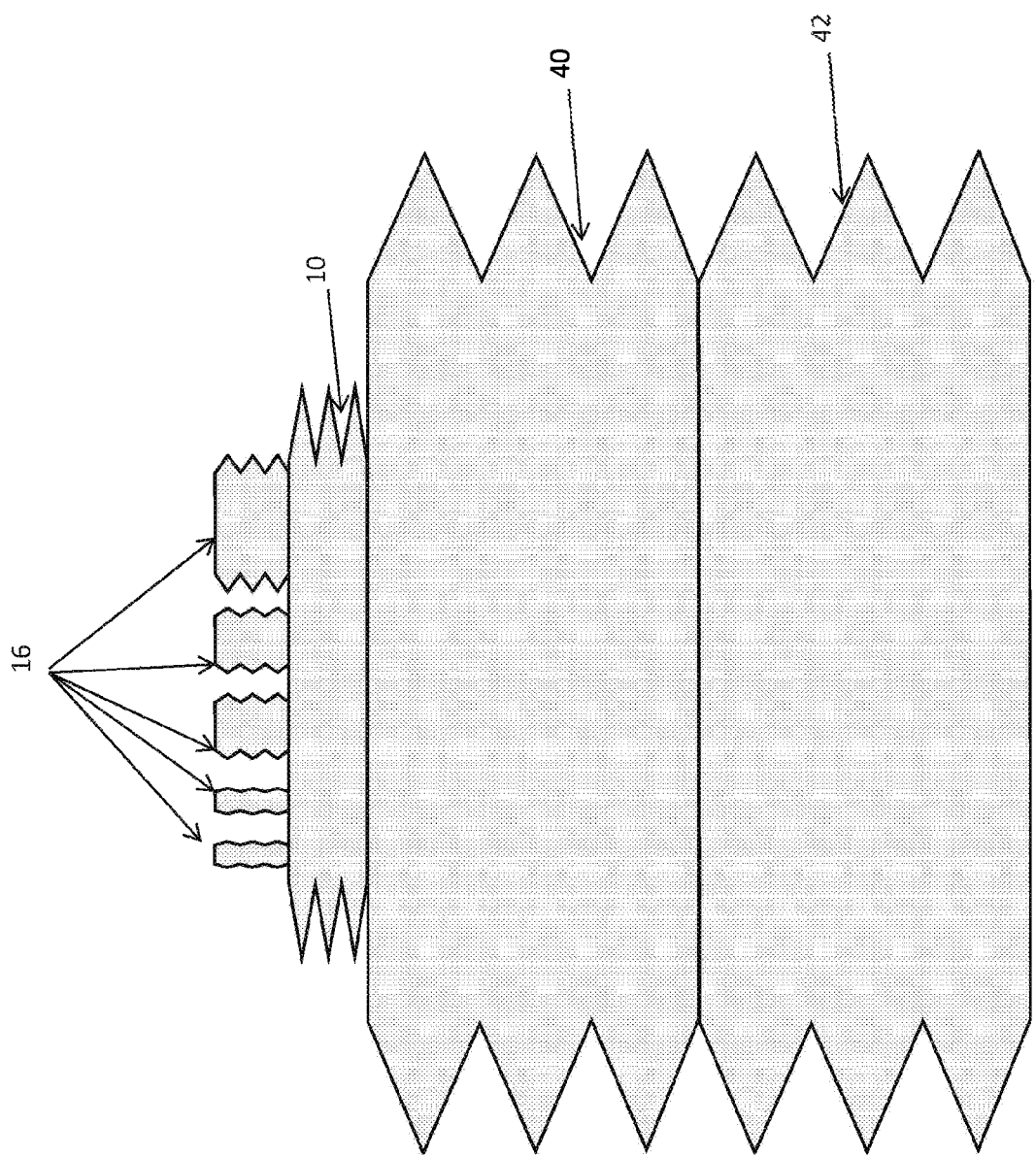
FIG. 4 shows a device of the present invention having a primary container combined with one or more further containers such as a bioreactor.

FIG. 4 shows how a set of containers of the invention may be configured. Thus, a primary container (10) is in direct fluid communication with a plurality of auxiliary containers (16) arranged in parallel. The primary container (10) is itself in fluid communication with a first further container such as a bioreactor (40) and a second further container such as a bioreactor (42). It will be understood that the primary container (10) and the first and second containers (40, 42) are arranged in series.

Figure 5:
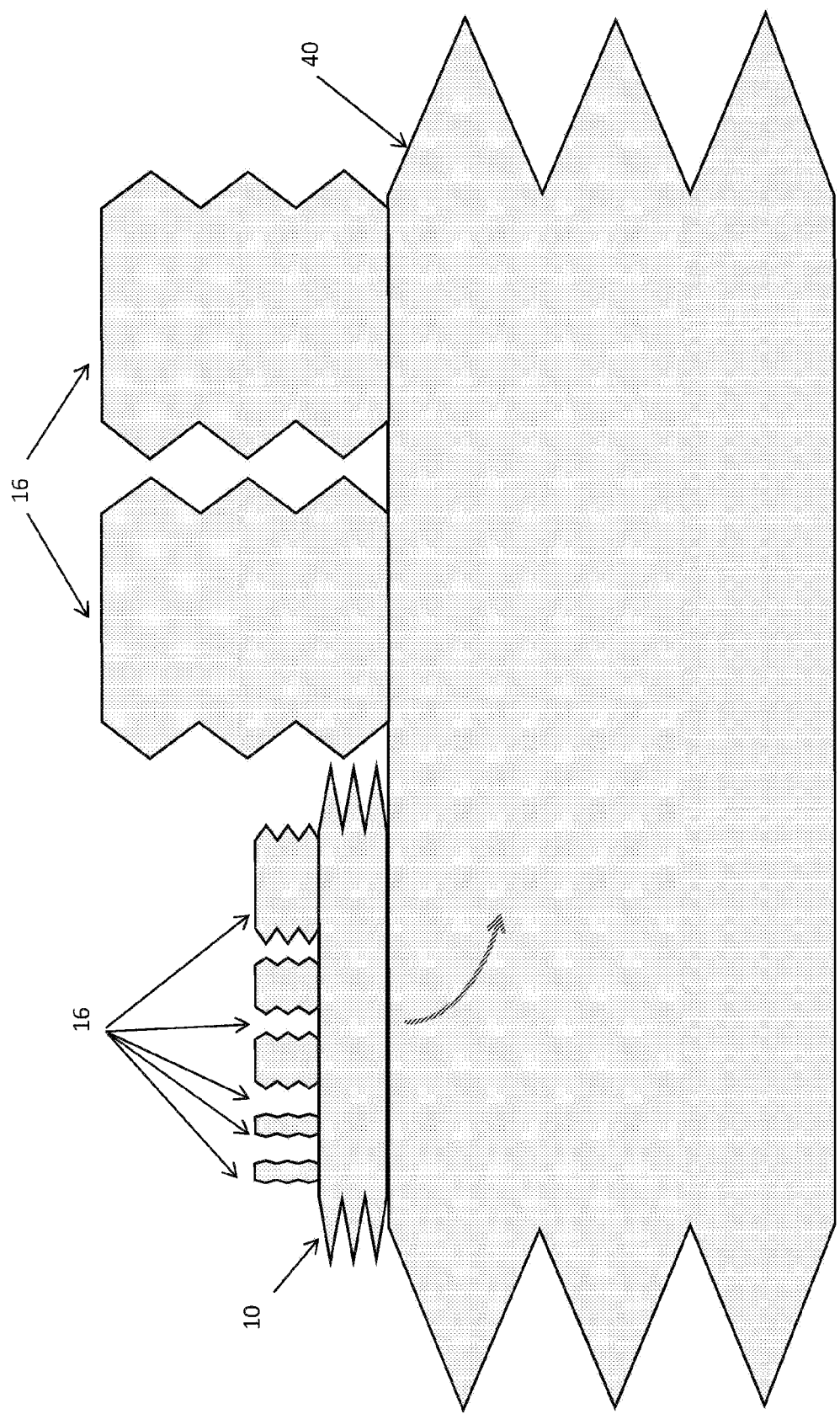
FIG. 5 shows a different arrangement of the device of the invention from that of FIG. 4, where some auxiliary containers are in direct fluid communication with the primary container, and further auxiliary containers are in direct fluid communication with the further container.

FIG. 5 shows a variant configuration of FIG. 4. In FIG. 5, a primary container (10) is in direct fluid communication with a plurality of auxiliary containers (16) arranged in parallel. The primary container (10) is itself in fluid communication with a further container such as a bioreactor (40)

In both FIG. 4 and FIG. 5, the primary container (10) is used for small scale processing and initial startup (e.g. genetic modification) of the cell culture, with the auxiliary containers (16) being used as the feeds and wastes for this process. Once the small scale initial processing is completed, the cells can be transferred from the primary container (10) into a first bioreactor (40) for large scale processing (e.g. growth and culture/harvesting).

FIG. 5 differs in that it shows a means for carrying out further processing of the medium once it has been transferred into the bioreactor (40). Thus, further auxiliary containers (16) are arranged to be in direct fluid communication with the bioreactor (40) but not with the primary container (10). These further auxiliary containers (16) are configured to hold feeds or accept waste from the large scale processes that take place in the bioreactor (40). Accordingly, FIG. 5 shows how two parallel processes may be conducted in series using the device of the present invention.

Figure 6:
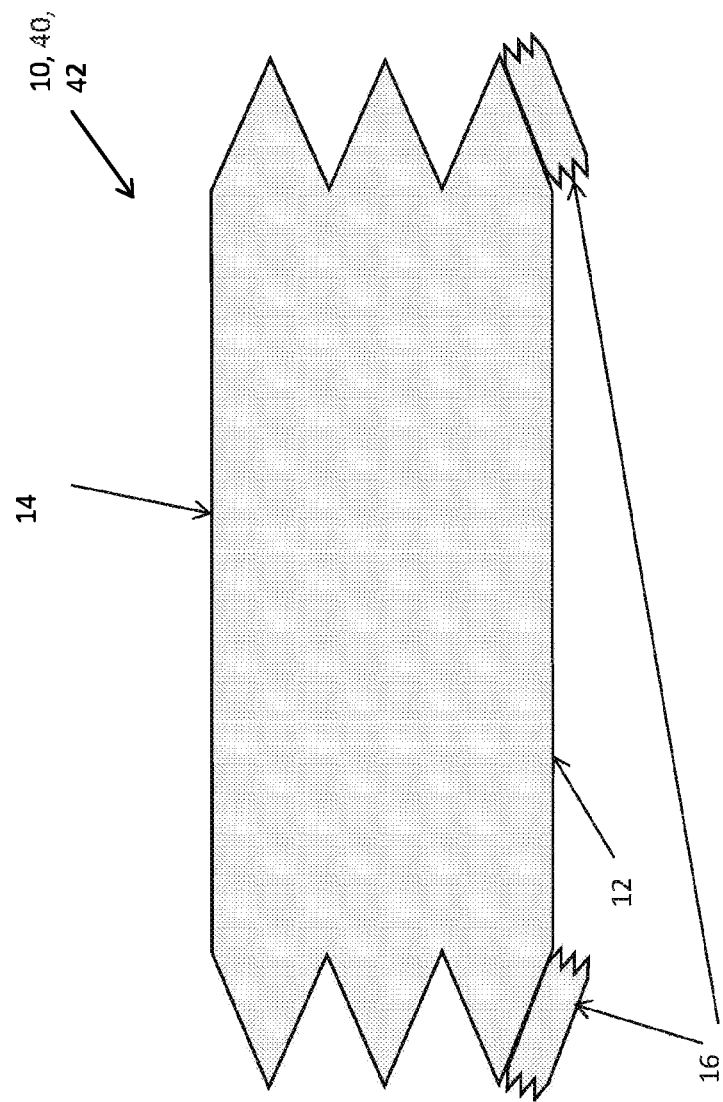
FIG. 6 shows how one or more auxiliary containers might be connected at a point other than the top of a container of the invention. Such a connection at or towards the base of a container of the invention might be used e.g. for sampling (for quality analysis or quality control purposes) or for collecting the final product of the cell culture.
Figure 8A:
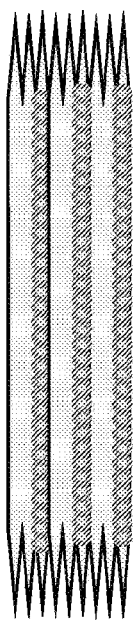
Figure 8B:
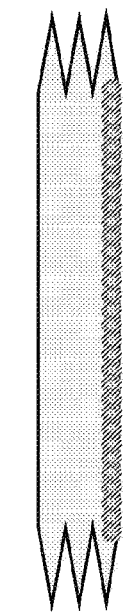
Figure 8C:
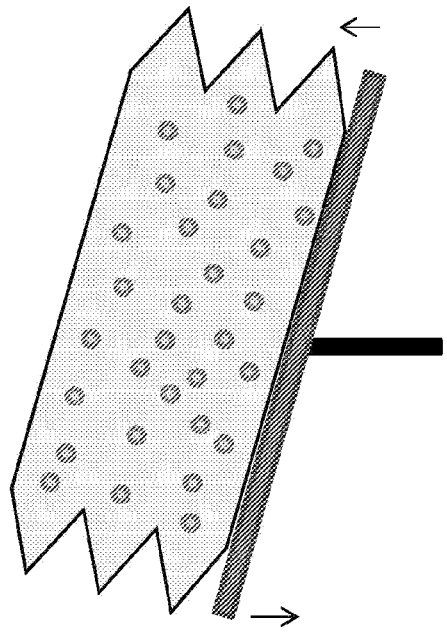
Figure 8D:
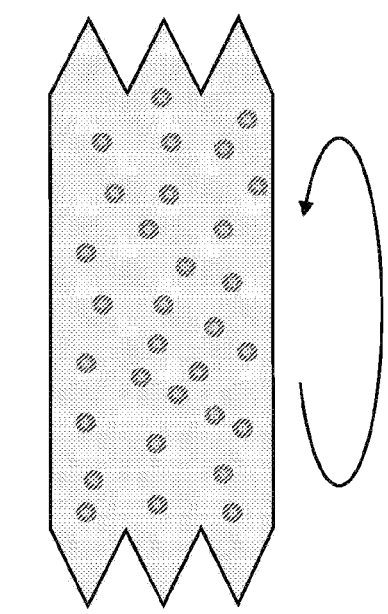

As shown in FIG. 6, the auxiliary containers (16) need not be disposed on the top section (14) of the primary container (10), or the first further container (40) or the second further container (42). They may in one configuration be disposed at the base section (12) of the container (10, 40, 42).

This permits e.g. easy sampling of any centrifuged product, or collection thereof. It will be understood that auxiliary containers (16) may be disposed in both configurations, i.e. disposed at the base section (12) as well as at the top section (14) of the container (10, 40, 42).

It will be understood from the statements of the invention provided herein that an advantage of having auxiliary containers (16) which are in fluid communication with the primary container (10) but separable therefrom is that the conditions within the auxiliary containers (16) may be maintained at a different environment from that of the primary container (10). Thus, while in FIG. 7(a), the primary container (10) may be maintained at the same temperature as the auxiliary containers (16), FIG. 7(b) shows that the auxiliary containers (16) may be kept at different temperatures e.g. by means of insulated sleeves (60). In this configuration, three auxiliary containers (16) are maintained at refrigerated or frozen temperatures (e.g. 4 degrees Celsius and minus 20 degrees Celsius, respectively) while two auxiliary containers (16) are maintained at ambient temperature, while a further means (not shown) can maintain the primary container (10) at optimum cell culture temperature such as 37 degrees Celsius.

It will be understood further from FIG. 8 that the device of the invention can contain other means for movement of the primary container (10). Thus, spinning/centrifuging and/or rocking of the primary container are all envisaged.

It will also be understood from FIG. 9 that the auxiliary containers (16) may have fluid communication to the primary container (10) in different directions. Thus, in order to keep the cells (80) in suspension within the primary container (10) at optimal conditions, media can be introduced into the primary container from a first auxiliary container (16a), with waste media being collected into a second auxiliary container (16b). As stated herein, compression of the primary container in an upwards direction will force the waste media into the auxiliary container (16b).

An exemplary method of using the device of the invention in multi-step operations (e.g. transduction, activation, expansion and washing of CAR-T cell therapies) will now be described with reference to FIG. 10. Starting at FIG. 10(a), the cells (80) are in suspension within a primary container (10). A number of auxiliary containers (16(a) to 16(d)) are configured to hold various feeds and media; while a further auxiliary container configured to hold waste (16(e)) is initially compressed and empty.

Figures 10E, 10F, 10G, 10H:
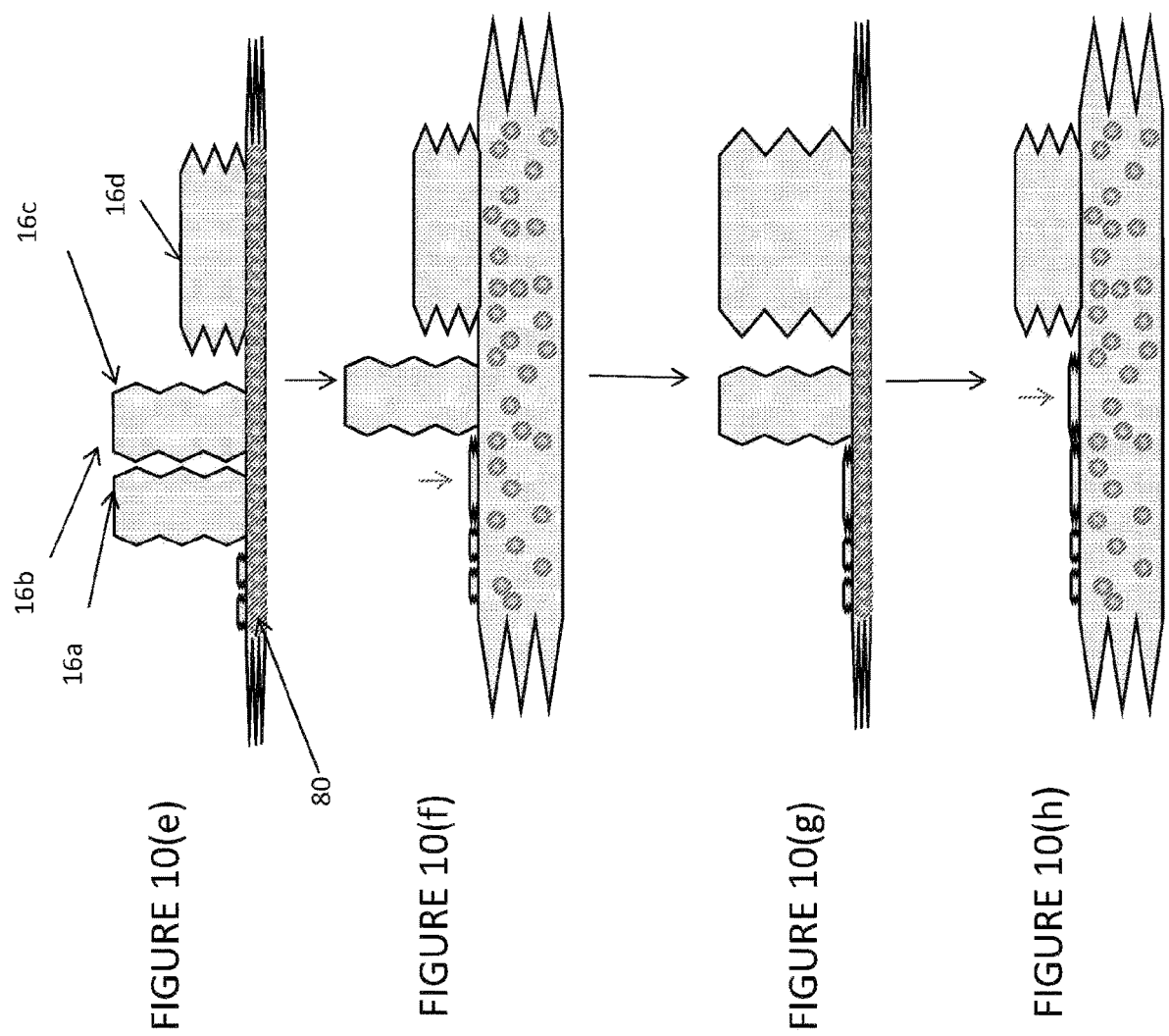

In FIG. 10(b), it can be seen that the first auxiliary container containing e.g. a viral vector medium (16(a)) has been emptied into the primary container (10) and that the cells (80) are suspended in the medium. Once the vector has had sufficient time to incubate, the primary container is centrifuged and the cells (80) are deposited on the base of the primary container (10). FIG. 10(c) shows that the primary container is emptied into the waste auxiliary container (16(e)) to remove the spent medium. As shown in FIG. 10(d), the cells can then be washed in a further medium, e.g. containing cell activation factors, which is introduced into the primary container (10) from a further auxiliary container (16(b)). As shown in FIG. 10(e), the primary container (10) is then subjected to further centrifugation and the primary container (10) is then emptied into the waste auxiliary container (16(e)). The primary container (10) should now have no or minimal traces of the viral vector. Following this, FIG. 10(f) shows introduction of a further medium (e.g. expansion medium) into the primary container (10) from a further auxiliary container (16(c)). Once the cells have been incubated for a sufficient time, the primary container (10) can be centrifuged again (FIG. 10(g)) and the medium therein collected in the waste auxiliary container (16(e)). Fresh medium, e.g. formulation buffer, can then be introduced from a further auxiliary container (16(d)) (FIG. 10(h)) and the cells resuspended.

It will be understood therefore that the cells in the primary container (10) may be maintained for as long as required. Where the auxiliary containers (16) are detachable, fresh auxiliary containers having additional media may be connected in place of spent auxiliary containers; and/or the waste auxiliary container (16(e)) may be detached for emptying and either it or a fresh waste auxiliary container may be subsequently reconnected.

The methodology show in FIG. 10 may be carried out within a device as shown e.g. in FIG. 4. In other words, once the reaction in the primary container (10) is complete, the cells may be transferred by emptying (e.g. via compression) the primary container (10) into a further container (40) such as a bioreactor. It may therefore be desirable to close off the used primary container (10) to prevent it from contaminating the further container (40).

In such a case, the valve arrangement as shown in FIG. 11 may be used. FIG. 11(a) shows a container of the invention, which may be a primary container (10), an auxiliary container (16) or a further container (40, 42). The container (10, 16, 40, 42) is shown in a non-closed state, and it has two ports (110, 112) on opposed sides. As shown in FIG. 11(a) the two ports (110, 112) are on the top section and the base section. It can also be seen in FIG. 11(a) that one of the ports (110) comprises a valve member (115) which extends into the container (10, 16, 40, 42) and is configured to interact with the other port (112). The interaction is shown in FIG. 11(b), where the container (10, 16, 40, 42) is fully compressed and the valve member (115) extends from the first port (110) into the second port (112), thereby creating a bypass so that any fluid passing through the first port (110) and the second port (112) will not enter the container (10, 16, 40, 42). FIG. 11(c) shows an optional detail of FIG. 11(b), wherein the valve member (115) is fitted with a locking mechanism (in this case, hooks) (119) which form a one-way connection and interlock between the first port (110) and the second port (112). In this way, a water-tight connection may be formed.

It can be seen from the schematic of FIG. 11(d) that this arrangement may be used to bring two containers (A, C) into direct fluid communication even where there is an intermediate container (B) between them. Compression of the intermediate container (B) and the use of a locking valve (115) as previously described means that any fluid can pass directly from the first container (A) into the further container (C) without entering the intermediate container (B). For example, the first container (A) may be an auxiliary container of the invention, the intermediate container (B) may be a primary container of the invention, and the further container (C) may be a bioreactor. Thus, once the initial cell setup is complete and the cells are transferred into the bioreactor (C) for further culturing, it is still possible to introduce materials (e.g. fresh culture medium) or extract materials (e.g. harvested cell products, spent culture medium) into or from auxiliary container (A) directly with the bioreactor (C). FIG. 11(d) also shows that the valve arrangement (115) shown in FIGS. 11(a) to 11(c) can permit fluid flow in either direction. It will be understood that in some cases it may be preferred for fluid flow to be unidirectional, as discussed in more detail herein.

As described in detail herein, a container of the invention may be constructed of different materials. As shown in FIG. 12, a container of the invention (10, 16, 40, 42) may have a removable base plate (120) enabling a different material to be connected depending on the intended use of the container (10, 16, 40, 42). For example, removable base plates mean that the cell culture surface can be adapted. Thus, a cell culture tissue plastic of choice for the relevant cell type being cultured can be attached to the cell. In FIG. 12(b), the base has been removed and a new base plate (120), constructed of a particular material, is then attached to the container (10, 16, 40, 42). For example the resulting container, shown in FIG. 12(c), may have improved gas transfer to cells through inclusion of a thin film gas permeable sheet or membrane. This may be of use in culturing settled suspension cells, e.g. T-cells. The base plate (120) may have rigid support strips (125) and this may be of particular value where the base plate (120) is constructed of a thin film, to ensure structural integrity of the base plate (120). The base plate (120) may have a port (128) which may be configured as described for FIG. 11 above, i.e. to interact with a further port on the opposed surface of the container (10, 16, 40, 42).

As shown in FIG. 13, a container of the invention (10, 16, 40, 42) may be configured with sensors to monitor the contents of the container. A variety of sensor options are possible and may be used individually or in combination as required. For example, an optical probe (120) may be connected to permit examination by microscope; an optical density probe (121) may be connected to establish e.g. optical cell density of a cell culture. Oxygen/pH probes (122) may be connected to oxygen/pH sensor spots (123) in the inside wall of the container (10, 16, 40, 42). It will be readily understood that the use of sensors is well understood and that the skilled reader may apply any such means as are known in the art.

As described herein, the device of the invention may include means for separating out cells within a culture from the medium within which they are grown. FIG. 14 shows two ways in which a cell culture (80) within a container of the invention (10, 16, 40, 42) may be spun out. FIG. 14(a) shows a conventional centrifugation, where the cells are pelleted and lie on the base of the container (10, 16, 40, 42). FIG. 14(b) shows the results of a different methodology, whereby the cells are spun such that they coat the walls of the container (10, 16, 40, 42). In the alternative, FIG. 14(c) shows that a container of the invention (10, 16, 40, 42) may be subdivided by means of a filter membrane (140). Compressing or collapsing (or partially collapsing) the container (10, 16, 40, 42) means that the cells (80) are trapped within one portion of the container via the filter membrane (140) while the medium is ejected out into the other part of the container, as shown in FIG. 14(d).

An alternative means for separating the waste medium from the cells is shown in FIG. 15. In this configuration, the container of the invention (10, 16, 40, 42) is provided with a length of piping (151) which connects an auxiliary container (16) with the medium (155). The piping (151) may be collapsible in the same manner as the container (10, 16, 40, 42), i.e. it should not prevent compression and collapse of the container (10, 16, 40, 42). The piping (151) has an opening (152) at a specific height which enables the spent medium (155) to be forced into the piping (151) when the container (10, 16, 40, 42) is compressed. FIG. 15(a) shows the arrangement when the cells (80) are spun so as to be plated onto the sides of the container (10, 16, 40, 42). In this embodiment, the opening (152) is as close to the base of the container (10, 16, 40, 42) as is practicable: compression of the container (10, 16, 40, 42) forces the medium (155) up into a suitably configured auxiliary container (16(c)). If required, fresh culture medium, washing buffer, etc. can be introduced from other auxiliary containers (16(a), 16(b)). In the alternative, the container (10, 16, 40, 42) may be centrifuged such that the cells (80) are pelleted out on to the base of the container (10, 16, 40, 42). In this configuration, the piping (151) has an opening (152) positioned above the level of the pelleted cells (80) such that compression of the container (10, 16, 40, 42) forces the spent medium (155) up into a suitably configured auxiliary container (16(c)) while leaving the cells (80) behind.

FIG. 15 also shows that a container of the invention (10, 16, 40, 42) may be provided with a gas vent (159) which can be used to establish gas/liquid phases within the container (10, 16, 40, 42), providing e.g. oxygen and/or carbon dioxide. This vent (159) is not limited to the embodiment shown in FIG. 15 and may be incorporated into the other embodiments shown in the other figures.

As described herein, a device of the invention may comprise a magnet to assist with purification of the cells. Such an arrangement is shown in FIG. 16, where the device (not shown) includes a magnet (160) which is located beneath the base plate of a container such as the primary container (10). In FIG. 16(a), the cells (80) are in suspension and an auxiliary container (16(a)) contains magnetic beads which are configured (e.g. via conjugation to a suitable moiety) to selectively bind to certain cells (e.g. those cells which have been successfully transfected to express a protein of interest). The magnet (160) at this point is not switched on. FIG. 16(b) shows the configuration once the magnetic beads have been transferred from the auxiliary container (16(b)) into the primary container (10). The beads make contact with and selectively bind to the cells of interest but not to those cells which e.g. have not been successfully transfected.

At this point, the magnet (160) is switched on and the results are as shown in FIG. 16(c): the cells bound to magnetic beads are drawn toward the magnet while those cells not bound to magnetic beads (the unbound cells) remain in suspension. Compression of the primary container (16) forces the spent medium and the unbound cells into a further auxiliary container (16(d)). A further auxiliary container (16(b)) containing wash buffer may be partially compressed at this point, allowing the cells to remain in partial suspension. Following this, as shown in FIG. 16(d), the unbound cells are separated from the bound cells, with the bound cells remaining in the primary container (10). As shown in FIG. 16(e), a further auxiliary container (16(c)) containing dissociation buffer is then compressed, transferring the dissociation buffer into the primary container (10). The dissociation buffer releases the bound cells from the magnetic beads and these cells are then released into suspension, as shown in FIG. 16(f). Additional wash buffer is transferred into the primary container (10) from an auxiliary container (16(b)), following which the primary container (10) is compressed, being emptied into a further auxiliary container (16(e)) to collect the target cells of interest, as shown in FIG. 16(g).

Another means for holding cells in position, e.g. so that they can be washed, is shown in FIG. 17. A container (10, 16, 40, 42) of the invention holds cells (80) in place via means of acoustic wave generators (170). The acoustic wave (171) holds cells in place within the container (10, 16, 40, 42) without the need for filters or centrifugation. This may permit a continuous washing process, with arrows indicating the direction of the washing buffer.

FIG. 18 discloses the use of a container of the invention in collecting blood. Blood from a blood source (180), which can be a placenta with umbilical chord, or a vein, or other appropriate source, is collected in one or more drains (181) which lead into a flow regulator (182). The flow regulator may be a simple clip or it may be a vacuum/stepper motor to assist flow into a container such as an auxiliary container of the invention (16). The container (16) is initially fully compressed, empty and sterile; it is connected up via the flow regulator (182) to the blood drains (181). Flow of blood into the container can be vacuum assisted or via stepper motor controller, as previously discussed. Once full, the container (16) is disconnected and can be frozen and shipped to a central storage facility (not shown).

FIG. 19 shows processing of blood once collected. In FIG. 19(a) a first auxiliary container (16(a)) is connected to a primary container (10). One or more further auxiliary containers are also connected to the primary container (10) at a position (16(b)) between the first auxiliary container (16(a)) and the primary container (10) but are fully closed and not in fluid connection with the first auxiliary container (16(a)). The first auxiliary container (16(a)) holds blood taken from a donor or patient or other source. FIG. 19(a) shows the transfer of blood from the first auxiliary container (16(a)) into the primary container (10) via compression/collapse of the first auxiliary container (16(a)). In FIG. 19(b), the primary container (10) is spun so as to fractionate the various portions of the blood into vertical columns of plasma (190), stem cells (191) and red blood cells (192). It can be seen in FIG. 19(b) that the first auxiliary container (16(a)) is fully collapsed. It may subsequently be removed.

FIG. 19(c) shows that an auxiliary container (16(c)) is filled with the plasma (190) via compression of the primary container (10) and/or via opening of the auxiliary container (16(c)) thereby drawing in the fluid from the primary container (10). Once the plasma fraction (190) is fully removed from the primary container (10), a further auxiliary container (16(d)) can be filled with the stem cell fraction (191) as shown in FIG. 19(d). Following this the red blood cells (192) can also be collected into a further auxiliary container (not shown). As an alternative, FIG. 19(e) shows an embodiment where the red blood cells (192) are retained in a suitably configured primary container (10).

Following separation, the various fractions can be used, stored, frozen etc. as required (not shown).

FIG. 20 shows a variant on the process of FIG. 19. FIG. 20(a) a first auxiliary container (16(a)) is connected to a primary container (10). One or more further auxiliary containers are also connected to the primary container (10) at a position (16(b)) between the first auxiliary container (16(a)) and the primary container (10) but are fully closed and not in fluid connection with the first auxiliary container (16(a)). The first auxiliary container (16(a)) holds blood taken from a donor or patient or other source. FIG. 20(a) shows the transfer of blood from the first auxiliary container (16(a)) into the primary container (10) via compression/collapse of the first auxiliary container (16(a)). In FIG. 20(b), the primary container (10) is spun so as to fractionate the various portions of the blood into horizontal columns of plasma (190), stem cells (191) and red blood cells (192). It can be seen in FIG. 20(b) that the first auxiliary container (16(a)) is fully collapsed. It may subsequently be removed.

FIG. 20(c) shows that an auxiliary container (16(c)) is filled with the plasma (190) via compression of the primary container (10) and/or via opening of the auxiliary container (16(c)) thereby drawing in the fluid from the primary container (10). Once the plasma fraction (190) is fully removed from the primary container (10), a further auxiliary container (16(d)) can be filled with the stem cell fraction (191) as shown in FIG. 20(d). Following this the red blood cells (192) can also be collected into a further auxiliary container (not shown). As an alternative, FIG. 20(e) shows an embodiment where the red blood cells (192) are retained in a suitably configured primary container (10).

Following separation, the various fractions can be used, stored, frozen etc. as required (not shown).

FIG. 21 shows an alternative arrangement for transferring/closing off fluid communication between a plurality of linked containers. As shown in FIG. 21(a), a first container (211) is in the collapsed state, and adjoined to a second container (212), also in the collapsed state. A third container (213), joined to the second container (212), is opened and contains a cell culture. A conical insert (210) is connected to a central opening in the first container (211) and extends through concentric openings in the second container (212) and the third container (213). The sides of the conical insert (210) are arranged such that the insert (210) enables fluid communication only between the exterior of the containers and the interior of the third container (213): there is no fluid communication into either the first container (211) or the second container (212) while both are in the closed position.

FIG. 21(b) shows that opening the second container (212) means that the conical insert (210) can be positioned so as to permit fluid communication between the second container (212) and the third container (213) but not with the first container (211). As shown in FIG. 21(c), once the contents of the third container (213) have been transferred to the second container (212), the third container (213) can be collapsed into a closed state, thereby shutting off communication into the third container (213). The conical insert (210) will now permit fluid communication only with the second container (212) and the outside of the containers, but not into the first (211) or third (213) containers.

FIG. 21(d) shows that opening the first container (211) means that the conical insert (210) can be positioned so as to permit fluid communication between the second container (212) and the first container (211) but not with the third container (213). As shown in FIG. 21(e), once the contents of the second container (212) have been transferred to the first container (211), the second container (212) can be collapsed into a closed state, thereby shutting off communication into the second container (212). The conical insert (210) will now permit fluid communication only with the first container (211), but not into the second (212) or third (213) containers.

Thus, an initial cell culture can be started in the third container (213) and successively transferred via the conical insert (210) into the other containers (212, 211).

The invention claimed is:

1. A device for use in growing, culturing and/or modifying cells, the device comprising a primary container having a first base section, a first top section arranged substantially in parallel with the first base section and a first wall element arranged between the first top section and the first base section and defining a corresponding internal lumen of the first primary container, in which the first wall element of the primary container is compressible with respect to the first top and first base sections, and in which the primary container has at least one optionally sealable inlet, in which the first wall element of the primary container is composed of a flexible material and includes one or more folds; and wherein the device further comprises one or more auxiliary containers, each auxiliary container in the one or more auxiliary containers couples with a respective inlet or outlet on the first top section of the primary container, wherein each auxiliary container in the one or more auxiliary containers is external to the primary container and in direct fluid communication with the primary container, and wherein the one or more auxiliary containers is located on the first top section of the primary container, and wherein the primary container or each auxiliary container in the one or more auxiliary containers comprises a valve.

2. The device of claim 1, wherein each auxiliary container in the one or more auxiliary containers comprises a second base section configured to detachably connect to the respective inlet or outlet of the primary container.

3. The device of claim 1, wherein each auxiliary container in the one or more auxiliary containers comprises a second base section, a second top section arranged substantially in parallel with the second base section and a second wall element arranged between the second top section and the second base section and defining a corresponding internal lumen of the auxiliary container, in which the second wall element of the auxiliary container is compressible with respect to the second top section and second base section, and in which the auxiliary container has at least one optionally sealable inlet, in which the second wall element of the auxiliary container is composed of a flexible material; and wherein the auxiliary container is configured to be detachably connected to the respective inlet or an outlet of the primary container.

4. The device of claim 1, wherein each auxiliary container in the one or more auxiliary containers comprises insulation configured to maintain the contents of that auxiliary container at a particular temperature.

5. The device of claim 1, wherein the primary container or an auxiliary container in the one or more auxiliary containers has the valve on each opposing side of the respective primary container or auxiliary container.

6. The device of claim 5, wherein each valve on the opposing sides of the respective primary container or auxiliary container are configured to interact by forming a channel when the respective primary container or auxiliary container is fully compressed.

7. The device of claim 1, wherein the device comprises a plurality of auxiliary containers.

8. The device of claim 1, wherein the one or more folds is one or more z-folds.

* * * * *